(12) United States Patent
Marshall et al.

(10) Patent No.: US 10,675,478 B2
(45) Date of Patent: Jun. 9, 2020

(54) EXTRAVASCULAR IMPLANTABLE ELECTRICAL LEAD HAVING UNDULATING CONFIGURATION

(71) Applicant: Medtronic, Inc., Minneapolis, MN (US)

(72) Inventors: Mark T. Marshall, Forest Lake, MN (US); Gonzalo Martinez, Mendota Heights, MN (US); Vladimir P. Nikolski, Blaine, MN (US); Nathan L. Olson, Shoreview, MN (US); Kevin R. Seifert, Forest Lake, MN (US); Teresa A. Whitman, Dayton, MN (US)

(73) Assignee: Medtronic, Inc., Minneapolis, MN (US)

( * ) Notice: Subject to any disclaimer, the term of this patent is extended or adjusted under 35 U.S.C. 154(b) by 1217 days.

(21) Appl. No.: 14/963,303

(22) Filed: Dec. 9, 2015

(65) Prior Publication Data

US 2016/0158567 A1    Jun. 9, 2016

Related U.S. Application Data

(60) Provisional application No. 62/089,417, filed on Dec. 9, 2014, provisional application No. 62/262,408, filed on Dec. 3, 2015.

(51) Int. Cl.
*A61B 5/042* (2006.01)
*A61N 1/05* (2006.01)
(Continued)

(52) U.S. Cl.
CPC .......... *A61N 1/3962* (2013.01); *A61B 5/0422* (2013.01); *A61N 1/05* (2013.01);
(Continued)

(58) Field of Classification Search
CPC ..... A61B 5/686; A61B 5/6879; A61B 5/6882; A61B 5/0422; A61B 5/6869;
(Continued)

(56) References Cited

U.S. PATENT DOCUMENTS 3,496,932 A   2/1970   Prisk et al.
4,030,509 A   6/1977   Heilman et al.
(Continued)

FOREIGN PATENT DOCUMENTS

WO    2009006331    1/2009

OTHER PUBLICATIONS (PCT/US2015/064606) PCT Notification of Transmittal of the International Search Report and the Written Opinion of the International Searching Authority, dated Apr. 25, 2016, 11 pages.
(Continued)

*Primary Examiner* — Lee S Cohen
*Assistant Examiner* — Erin M Cardinal
(74) *Attorney, Agent, or Firm* — Shumaker & Sieffert, P.A.

(57) ABSTRACT

This disclosure describes an implantable medical electrical lead and an ICD system utilizing the lead. The lead includes a lead body defining a proximal end and a distal portion, wherein at least a part of the distal portion of the lead body defines an undulating configuration. The lead includes a defibrillation electrode that includes a plurality of defibrillation electrode segments disposed along the undulating configuration spaced apart from one another by a distance. The lead also includes at least one electrode disposed between adjacent sections of the plurality of defibrillation sections. The at least one electrode is configured to deliver a pacing pulse to the heart and/or sense cardiac electrical activity of the heart.

23 Claims, 13 Drawing Sheets

(51) Int. Cl.
*A61N 1/39* (2006.01)
*A61B 5/00* (2006.01)

(52) U.S. Cl.
CPC ............ *A61N 1/0504* (2013.01); *A61B 5/686* (2013.01); *A61B 5/6882* (2013.01); *A61N 1/057* (2013.01); *A61N 1/0563* (2013.01)

(58) Field of Classification Search
CPC .. A61N 1/3962; A61N 1/0504; A61N 1/0563; A61N 1/056
See application file for complete search history.

(56) References Cited

U.S. PATENT DOCUMENTS

| | | | |
|---|---|---|---|
| 4,161,952 A | 7/1979 | Kinney et al. | |
| 4,355,646 A | 10/1982 | Kallok et al. | |
| 4,374,527 A | 2/1983 | Iversen | |
| 4,379,462 A | 4/1983 | Borkan et al. | |
| 4,628,934 A | 12/1986 | Pohndorf et al. | |
| 4,765,341 A | 8/1988 | Mower et al. | |
| 4,922,927 A | 5/1990 | Fine et al. | |
| 4,947,866 A | 8/1990 | Lessar et al. | |
| 4,991,603 A | 2/1991 | Cohen et al. | |
| 5,105,826 A | 4/1992 | Smits et al. | |
| 5,121,754 A | 6/1992 | Mullett | |
| 5,174,288 A | 12/1992 | Bardy et al. | |
| 5,176,135 A | 1/1993 | Fain et al. | |
| 5,203,348 A | 4/1993 | Dahl et al. | |
| 5,282,845 A | 2/1994 | Bush et al. | |
| 5,325,870 A | 7/1994 | Kroll et al. | |
| 5,336,253 A | 8/1994 | Gordon et al. | |
| 5,342,407 A | 8/1994 | Dahl et al. | |
| 5,387,233 A | 2/1995 | Alferness et al. | |
| 5,456,706 A | 10/1995 | Pless et al. | |
| 5,476,502 A | 12/1995 | Rubin | |
| 5,522,874 A | 6/1996 | Gates | |
| 5,531,782 A | 6/1996 | Kroll et al. | |
| 5,534,022 A | 7/1996 | Hoffmann et al. | |
| 5,545,183 A * | 8/1996 | Altman ................. | A61N 1/056 607/4 |
| 5,545,205 A | 8/1996 | Schulte et al. | |
| 5,654,030 A | 8/1997 | Munshi et al. | |
| 5,683,443 A | 11/1997 | Munshi et al. | |
| 5,800,465 A | 9/1998 | Thompson et al. | |
| 5,810,887 A | 9/1998 | Accorti, Jr. et al. | |
| 5,833,714 A | 11/1998 | Loeb | |
| 5,849,031 A | 12/1998 | Martinez et al. | |
| 5,871,531 A * | 2/1999 | Struble ................. | A61N 1/057 600/375 |
| 5,916,243 A | 6/1999 | KenKnight et al. | |
| 5,922,014 A * | 7/1999 | Warman ................. | A61N 1/056 607/122 |
| 5,922,024 A | 7/1999 | Janzen et al. | |
| 5,925,073 A * | 7/1999 | Chastain ................. | A61N 1/057 607/122 |
| 6,066,165 A | 5/2000 | Racz | |
| 6,256,541 B1 | 7/2001 | Heil et al. | |
| 6,321,123 B1 | 11/2001 | Morris et al. | |
| 6,327,498 B1 | 12/2001 | Kroll | |
| 6,345,198 B1 | 2/2002 | Mouchawar et al. | |
| 6,430,449 B1 | 8/2002 | Hsu et al. | |
| 6,658,289 B2 | 12/2003 | Helland | |
| 6,721,597 B1 | 4/2004 | Bardy et al. | |
| 6,721,598 B1 | 4/2004 | Helland et al. | |
| 7,047,086 B2 | 5/2006 | Taskiran et al. | |
| 7,313,444 B2 | 12/2007 | Pianca et al. | |
| 7,465,341 B2 | 12/2008 | Eliasson | |
| 7,668,601 B2 | 2/2010 | Hegland et al. | |
| 7,684,864 B2 | 5/2010 | Olson et al. | |
| 7,761,150 B2 | 7/2010 | Ghanem et al. | |
| 7,899,555 B2 | 3/2011 | Morgan et al. | |
| 7,917,216 B1 | 3/2011 | Ryu et al. | |
| 8,017,179 B2 | 9/2011 | Atanasoska et al. | |
| 8,498,721 B2 | 7/2013 | Scheiner et al. | |
| 9,855,414 B2 | 1/2018 | Marshall et al. | |
| 2002/0035377 A1 | 3/2002 | Bardy et al. | |
| 2002/0103507 A1* | 8/2002 | Helland ................. | A61N 1/0563 607/5 |
| 2002/0103523 A1 | 8/2002 | Helland et al. | |
| 2003/0050681 A1* | 3/2003 | Pianca ................. | A61N 1/056 607/125 |
| 2003/0088187 A1* | 5/2003 | Saadat ................. | A61B 5/015 600/547 |
| 2003/0105501 A1 | 6/2003 | Warman et al. | |
| 2003/0109914 A1* | 6/2003 | Westlund ................. | A61N 1/056 607/122 |
| 2005/0209646 A1 | 9/2005 | Wanasek | |
| 2005/0277990 A1 | 12/2005 | Ostroff et al. | |
| 2006/0020316 A1 | 1/2006 | Martinez et al. | |
| 2006/0041295 A1 | 2/2006 | Osypka | |
| 2006/0247753 A1 | 11/2006 | Wenger et al. | |
| 2007/0250142 A1 | 10/2007 | Francis et al. | |
| 2008/0046058 A1 | 2/2008 | Cross et al. | |
| 2008/0046059 A1 | 2/2008 | Zarembo et al. | |
| 2008/0195163 A1 | 8/2008 | Scharmer | |
| 2009/0248117 A1 | 10/2009 | Nippoldt et al. | |
| 2009/0264780 A1 | 10/2009 | Schilling | |
| 2009/0287266 A1 | 11/2009 | Zdeblick | |
| 2010/0063569 A1* | 3/2010 | Tockman ................. | A61N 1/056 607/125 |
| 2010/0114195 A1 | 5/2010 | Burnes et al. | |
| 2010/0121421 A1 | 5/2010 | Duncan et al. | |
| 2010/0198041 A1* | 8/2010 | Christian .......... | A61M 25/0074 600/375 |
| 2010/0198284 A1 | 8/2010 | Zhou et al. | |
| 2010/0305675 A1 | 12/2010 | Laske et al. | |
| 2012/0029335 A1 | 2/2012 | Sudam et al. | |
| 2012/0310239 A1* | 12/2012 | Stewart .............. | A61B 18/1492 606/41 |
| 2013/0023944 A1 | 1/2013 | Doerr | |
| 2013/0338730 A1 | 12/2013 | Shiroff et al. | |
| 2014/0052120 A1 | 2/2014 | Benscoter et al. | |
| 2014/0330327 A1 | 11/2014 | Thompson-Nauman et al. | |
| 2015/0142010 A1* | 5/2015 | Min ..................... | A61N 1/0551 606/129 |
| 2015/0306375 A1 | 10/2015 | Marshall et al. | |
| 2015/0306410 A1 | 10/2015 | Marshall et al. | |
| 2017/0266442 A1* | 9/2017 | Jackson ................. | A61N 1/3621 |

OTHER PUBLICATIONS (PCT/US2015/027478) PCT Notification of Transmittal of the International Search Report and the Written Opinion of the International Searching Authority, dated Jul. 10, 2015, 9 pages.
Ganapathy et al., "Implantable Device to Monitor Cardiac Activity with Sternal Wires," Pace, vol. 37, Dec. 2014, 11 pages.
Guenther et al., "Substernal Lead Implantation: A Novel Option to Manage DFT Failure in S-ICD patients," Clinical Research Cardiology, Published On-line Oct. 2, 2014, 3 pages.
Tung et al., "Initial Experience of Minimal Invasive Extra Cardiac Placement of High Voltage Defibrillator Leads," Canadian Cardiovascular Congress 2007, Oct. 2007, vol. 23, Supplement SC, Abstract 0697, http://www.pulsus.com/coc2007/abs/0697.htm, 2 pages.
O'Callaghan et al., "Current Status of Implantable Cardioverter-Defibrillators", Current Problems in Cardiology, vol. 22, No. 12, Dec. 1997, 66 pages.
Marshall, et al., "Extravascular Implantable Electrical Lead Having Undulating Configuration", JP Application No. 2017-528882, Office Action dated Dec. 23, 2019, English Translation, 2 pages.
Marshall et al., Extravascular Implantable Electrical Lead Having Undulating Configuration, CN Application No. 201580067249.7, First Office Action Dispatched Oct. 23, 2019, English Translation, 8 pages.

* cited by examiner

EXTRAVASCULAR IMPLANTABLE ELECTRICAL LEAD HAVING UNDULATING CONFIGURATION

CROSS-REFERENCE TO RELATED APPLICATION

This application claims the benefit of U.S. Provisional Application No. 62/089,417, filed on Dec. 9, 2014 and U.S. Provisional Application No. 62/262,408, filed on Dec. 3, 2015, the entire content of both of which is incorporated herein by reference in their entirety.

FIELD OF THE INVENTION

The present application relates to electrical stimulation leads and, more particularly, electrical stimulation leads having an undulating configuration for improved defibrillation, sensing, and/or pacing capabilities for use in extracardiovascular applications (e.g., subcutaneous or substernal applications).

BACKGROUND OF THE INVENTION

Malignant tachyarrhythmia, for example, ventricular fibrillation, is an uncoordinated contraction of the cardiac muscle of the ventricles in the heart, and is the most commonly identified arrhythmia in cardiac arrest patients. If this arrhythmia continues for more than a few seconds, it may result in cardiogenic shock and cessation of effective blood circulation. As a consequence, sudden cardiac death (SCD) may result in a matter of minutes.

In patients with a high risk of ventricular fibrillation, the use of an implantable cardioverter defibrillator (ICD) system has been shown to be beneficial at preventing SCD. An ICD system includes an ICD that is a battery powered electrical shock device, that may include an electrical housing electrode (sometimes referred to as a can electrode), that is coupled to one or more electrical lead wires placed within the heart. If an arrhythmia is sensed, the ICD may send a pulse via the electrical lead wires to shock the heart and restore its normal rhythm. Owing to the inherent surgical risks in attaching and replacing electrical leads directly within or on the heart, subcutaneous ICD systems have been devised to provide shocks to the heart without placing electrical lead wires within the heart or attaching electrical wires directly to the heart.

Electrical leads being utilized in subcutaneous systems typically include linear or curvilinear arrays of electrodes positioned on the lead body. Thus, the delivery of electrical stimulation therapy to the heart with current lead designs provides limited therapy vectors depending on the shape of the lead body, for which the electrical energy may impact the heart.

SUMMARY

This disclosure describes an implantable medical electrical lead and an ICD system utilizing the lead. The lead includes a lead body defining a proximal end and a distal portion, wherein at least a part of the distal portion of the lead body defines an undulating configuration. The lead includes a defibrillation electrode that includes a plurality of defibrillation electrode segments disposed along the undulating configuration spaced apart from one another by a distance. The lead also includes at least one electrode disposed between adjacent sections of the plurality of defibrillation sections. The at least one electrode is configured to deliver a pacing pulse to the heart and/or sense cardiac electrical activity of the heart.

In some instances, the plurality of defibrillation electrode segments are disposed along at least 80% of undulating configuration. In other instances, the plurality of defibrillation electrode segments are disposed along at least 90% of undulating configuration. The undulating configuration may include a plurality of peaks with a first portion of the plurality of peaks extending in a first direction away from a major longitudinal axis of the lead and a second portion of the plurality of peaks extending in a second, opposite direction away from the major longitudinal axis of the lead. The plurality of defibrillation electrode segments may, in some examples, be disposed along the first portion of the plurality of peaks and the at least one electrode may be disposed on the second portion of the plurality of peaks. In another example, the plurality of defibrillation electrode segments are disposed along at least one of the first and second portions of peaks and the at least one electrode is disposed along a segment of the undulating portion between peaks.

This application also provides an extravascular implantable cardioverter-defibrillator (ICD) system comprising an extravascular electrical stimulation lead and an ICD coupled to the extravascular electrical stimulation lead. The electrical stimulation lead includes a lead body defining a proximal end and a distal portion, wherein at least a part of the distal portion of the lead body defines an undulating configuration. The lead includes a defibrillation electrode that includes at least a first defibrillation electrode segment and a second defibrillation electrode segment disposed along the undulating configuration spaced apart from one another by a distance. The lead also includes at least one electrode disposed between the first and second defibrillation segments, the at least one electrode configured to, at least one of, deliver a pacing pulse to the heart and sense cardiac electrical activity of the heart.

This application also provides a method for implanting an extravascular electrical stimulation lead within a substernal location of a patient. The method includes creating an incision near a center of the torso of the patient, introducing an implant tool into the substernal location via the incision, and advancing the implant tool within the substernal location from the incision superior along a posterior of a sternum to form a substernal path. The method further includes introducing a distal portion of the lead into the substernal location. The lead includes a lead body defining a proximal end and the distal portion, wherein at least a part of the distal portion of the lead body defines a pre-formed undulating configuration, a defibrillation electrode that includes a plurality of defibrillation electrode segments disposed along the undulating configuration spaced apart from one another by a distance, and at least one electrode disposed between adjacent segments of the plurality of defibrillation segments, the at least one electrode configured to, at least one of, deliver a pacing pulse to the heart and sense cardiac electrical activity of the heart. The method includes advancing the distal portion of the lead through the substernal path, wherein the undulating configuration of the lead is in a relatively straight configuration when being advanced through the substernal path, and withdrawing the implant tool toward the incision to remove the implant tool from the body while leaving the lead in place along the substernal path. The distal portion of the lead takes its pre-formed undulating configuration within the substernal location as it exist the implant tool. The at least one electrode is disposed on the undulating configuration such that that undulating configuration pushes the at least one electrodes toward the left side of sternum compared to defibrillation electrode segments.

DETAILED DESCRIPTION

As used herein, relational terms, such as "first" and "second," "over" and "under," "front" and "rear," and the like, may be used solely to distinguish one entity or element from another entity or element without necessarily requiring or implying any physical or logical relationship or order between such entities or elements.

Figure 1A:
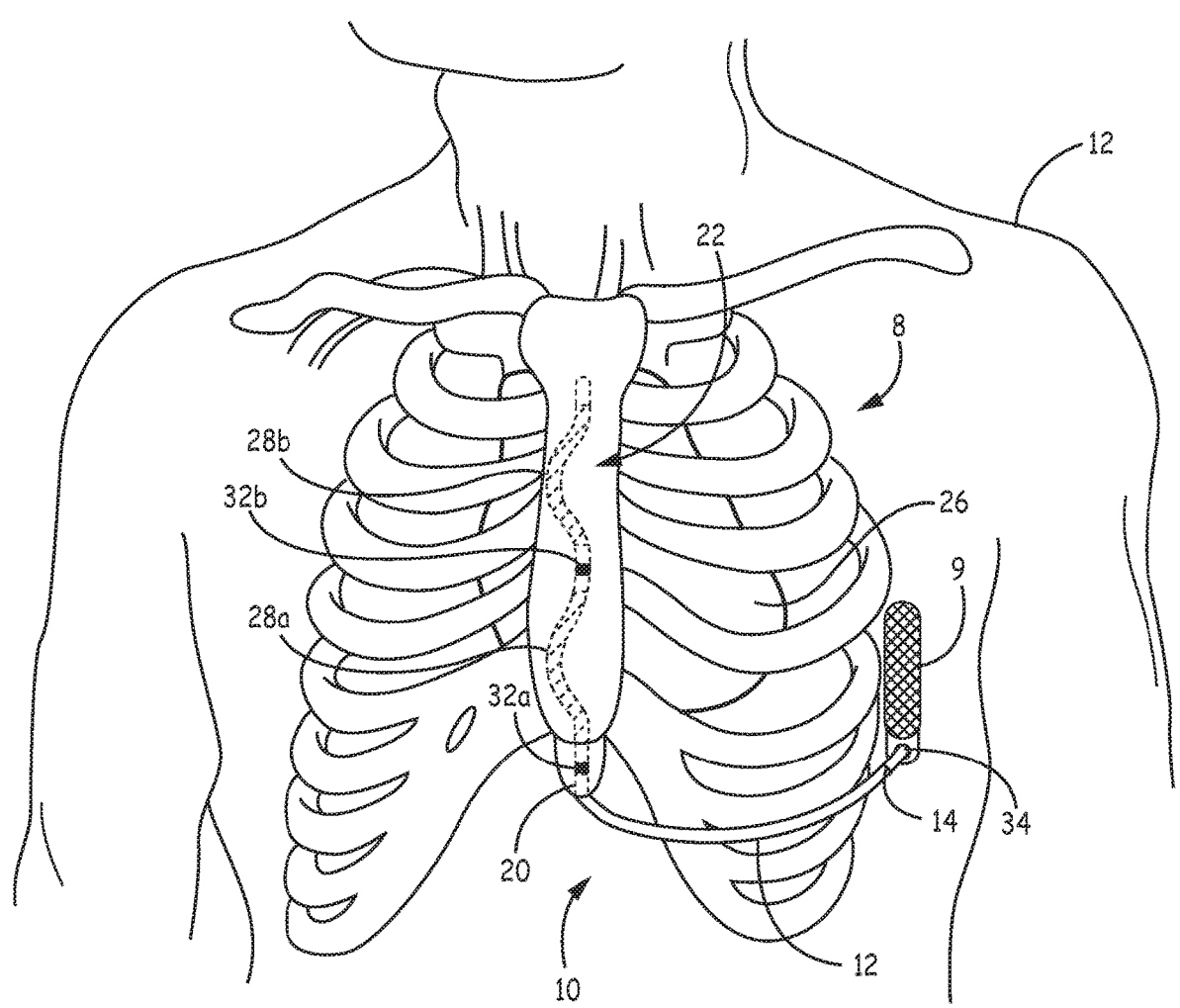
FIG. 1A is a front view of a patient implanted with the extracardiovascular ICD system implanted intra-thoracically.
Figure 1B:
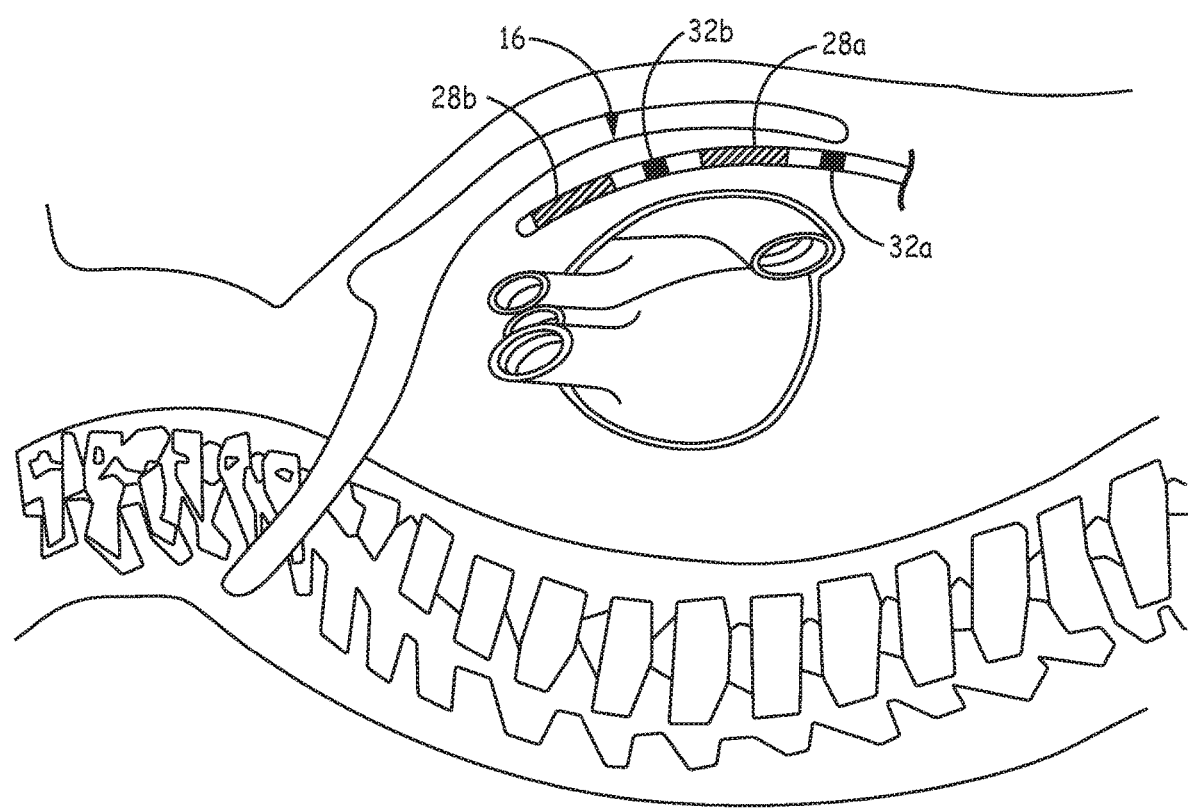
FIG. 1B is a side view of the patient implanted with the extracardiovascular ICD system implanted intra-thoracically.
Figure 1C:
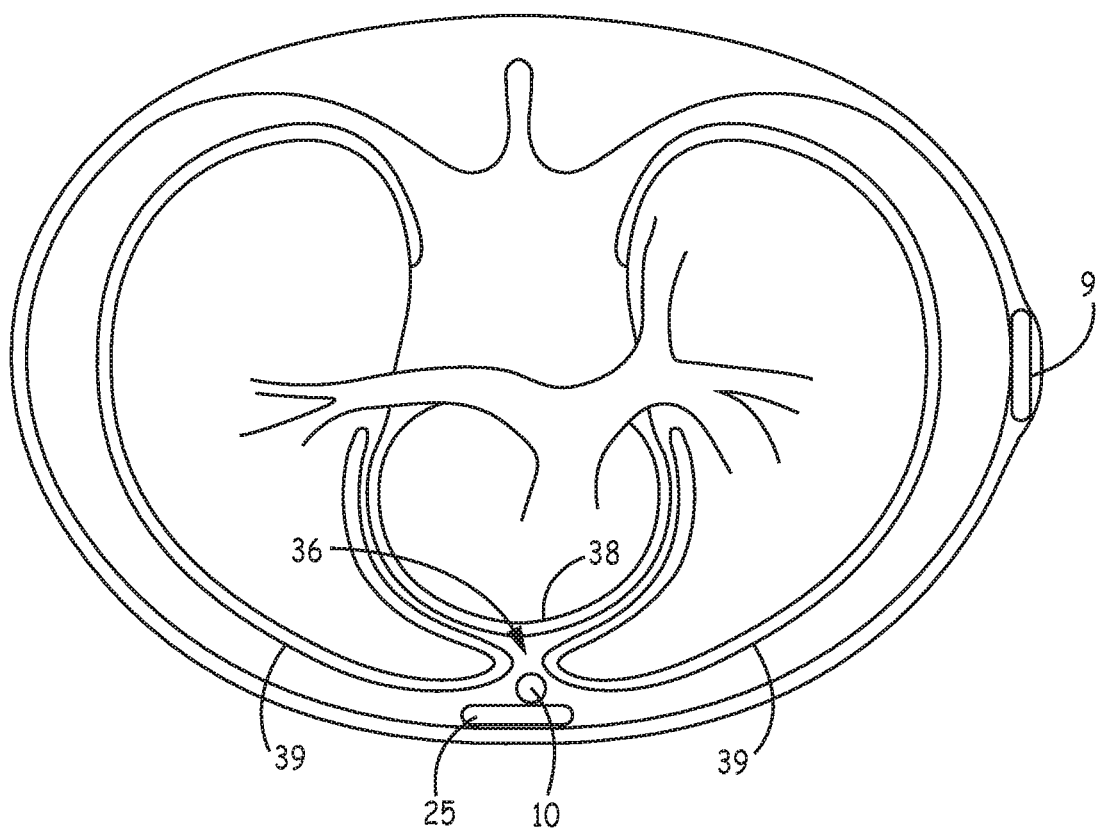
FIG. 1C is a transverse view of the patient implanted with the extracardiovascular ICD system implanted intra-thoracically.

Referring now to the drawings in which like reference designators refer to like elements, there is shown in FIGS. 1A-C and FIG. 2 are conceptual diagrams illustrating various views of an exemplary extracardiovascular implantable cardioverter-defibrillator (ICD) system 8. ICD system 8 includes an ICD 9 connected to a medical electrical lead 10 constructed in accordance with the principles of the present application. FIG. 1A is a front view of a patient implanted with the extracardiovascular ICD system 8. FIG. 1B is a side view of the patient implanted with the extracardiovascular ICD system 8. FIG. 1C is a transverse view of the patient implanted with the extracardiovascular ICD system 8.

The ICD 9 may include a housing that forms a hermetic seal that protects components of the ICD 9. The housing of the ICD 9 may be formed of a conductive material, such as titanium or titanium alloy, which may function as a housing electrode (sometimes referred to as a can electrode). In other embodiments, the ICD 9 may be formed to have or may include one or more electrodes on the outermost portion of the housing. The ICD 9 may also include a connector assembly (also referred to as a connector block or header) that includes electrical feedthroughs through which electrical connections are made between conductors of lead 10 and electronic components included within the housing of the ICD 9. As will be described in further detail herein, housing may house one or more processors, memories, transmitters, receivers, sensors, sensing circuitry, therapy circuitry, power sources and other appropriate components. The housing is configured to be implanted in a patient, such as the patient.

ICD 9 is implanted extra-thoracically on the left side of the patient, e.g., under the skin and outside the ribcage (subcutaneously or submuscularly). ICD 9 may, in some instances, be implanted between the left posterior axillary line and the left anterior axillary line of the patient. ICD 9 may, however, be implanted at other extra-thoracic locations on the patient as described later.

Figure 2:
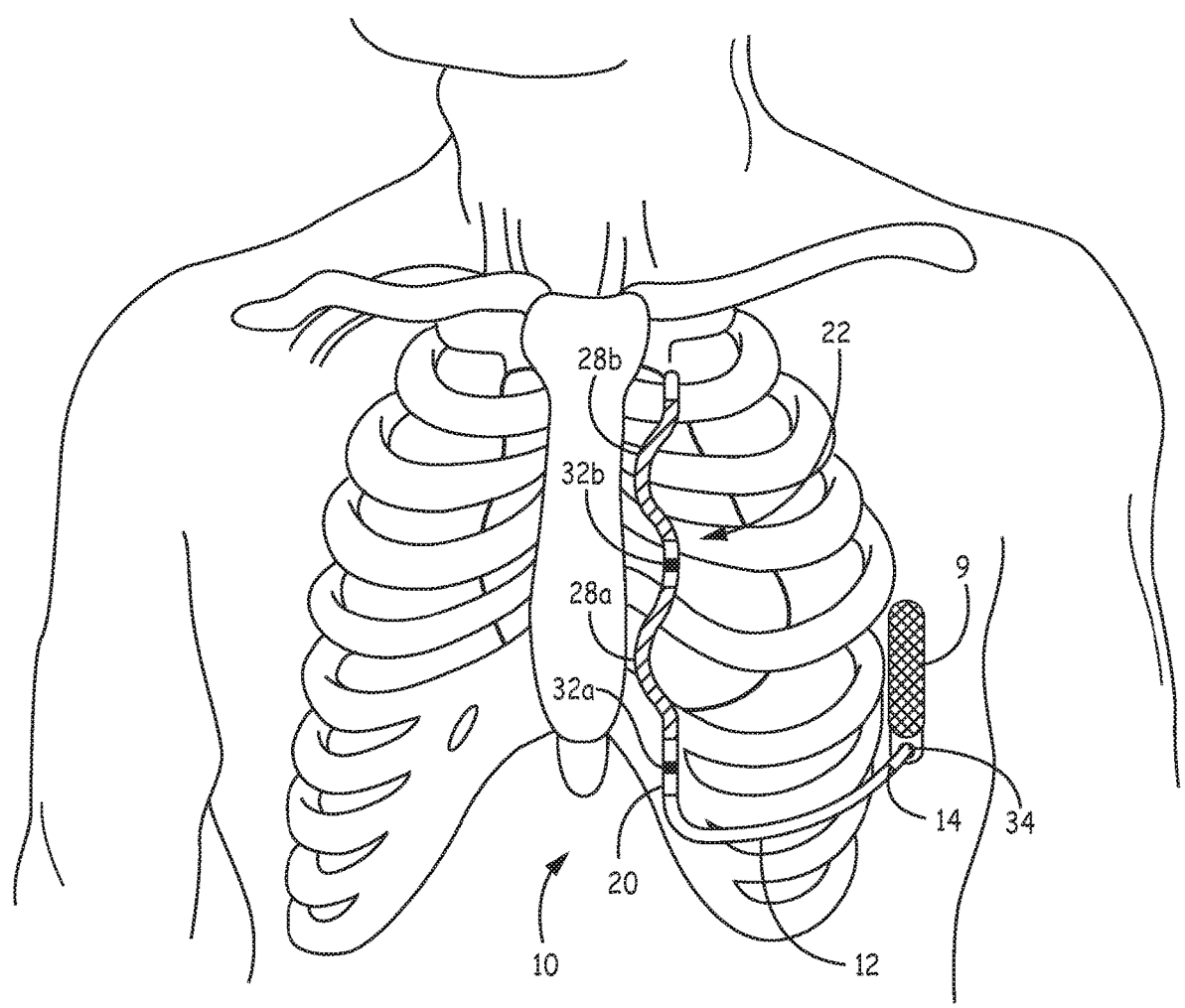
FIG. 2 is a front view of a patient implanted with the extracardiovascular ICD system implanted extra-thoracically.
Figure 3A:
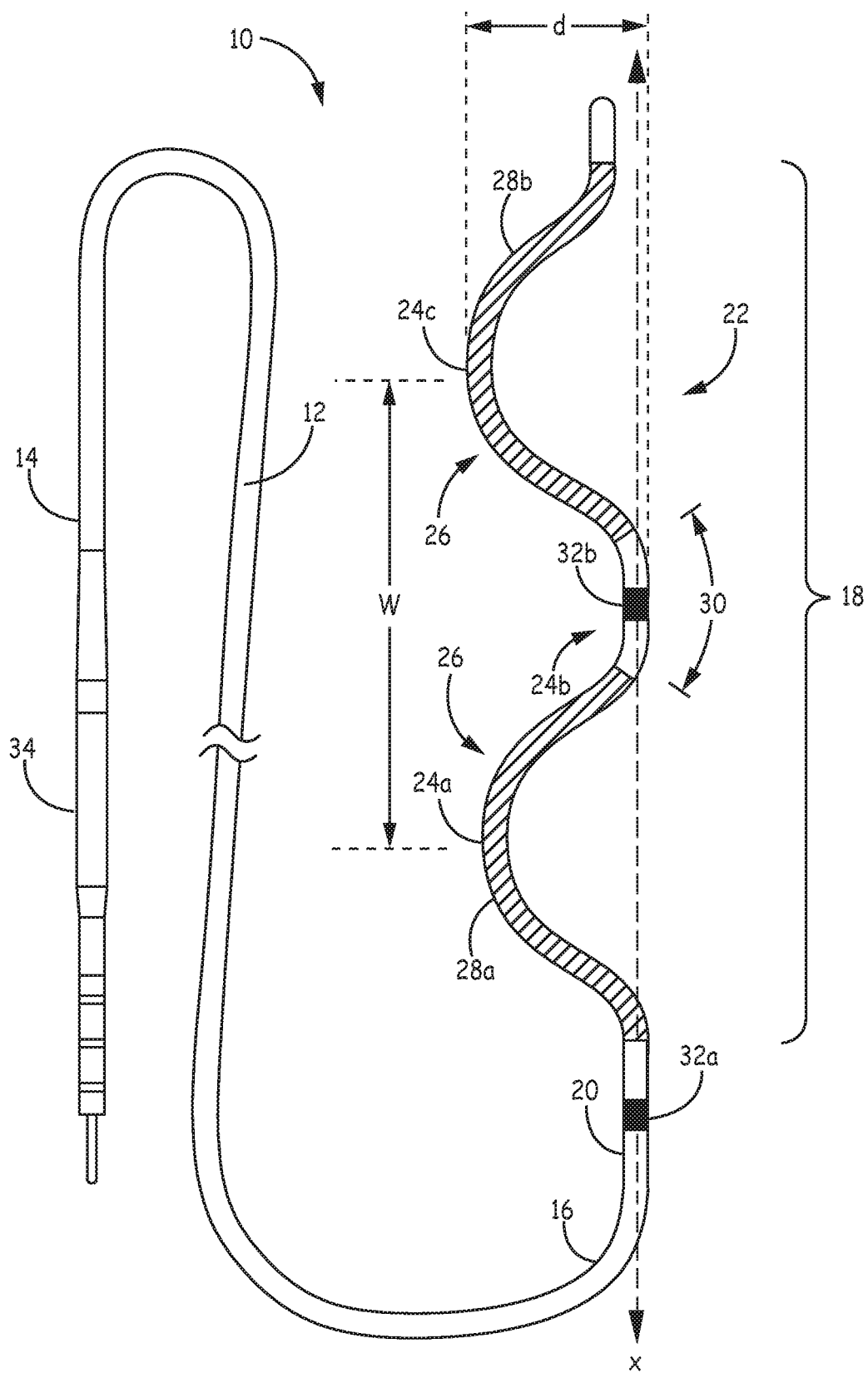
FIG. 3A is a schematic diagram illustrating an example lead constructed in accordance with the principles of the present application.
Figure 3B:
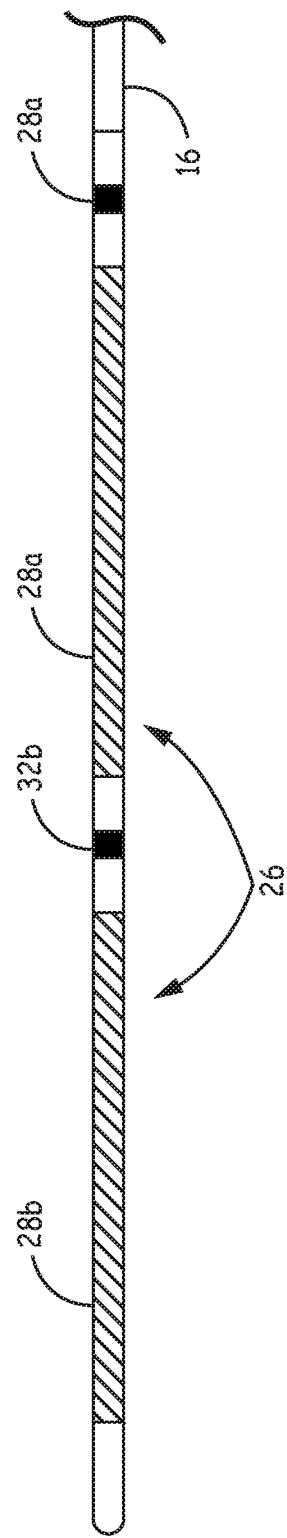
FIG. 3B is a schematic diagram illustrating an side view of the distal portion of the example lead of FIG. 3A.

FIGS. 3A and 3B are schematic diagrams illustrating various views of lead 10 in further detail. The lead 10 may include an elongated lead body 12 sized to be implanted in an extracardiovascular location proximate the heart, e.g., intra-thoracically (as illustrated in FIGS. 1A-C) or extra-thoracically (as illustrated in FIG. 2). For example, the lead 10 may extend extra-thoracically under the skin and outside the ribcage (e.g., subcutaneously or submuscularly) from ICD 9 toward the center of the torso of the patient, for example, toward the xiphoid process of the patient. At a position proximate xiphoid process, the lead body 12 may bend or otherwise turn and extend superiorly. In the example illustrated in FIGS. 1A-C, the lead body 12 extends superiorly intra-thoracically underneath the sternum, in a direction substantially parallel to the sternum. In one example, the distal portion 16 of lead 10 may reside in a substernal location such that distal portion 16 of lead 10 extends superior along the posterior side of the sternum substantially within the anterior mediastinum 36. Anterior mediastinum 36 may be viewed as being bounded laterally by pleurae 39, posteriorly by pericardium 38, and anteriorly by the sternum 22. In some instances, the anterior wall of anterior mediastinum 36 may also be formed by the transversus thoracis and one or more costal cartilages. Anterior mediastinum 36 includes a quantity of loose connective tissue (such as areolar tissue), adipose tissue, some lymph vessels, lymph glands, substernal musculature (e.g., transverse thoracic muscle), the thymus gland, branches of the internal thoracic artery, and the internal thoracic vein. In another example, e.g., illustrated in FIG. 2, the lead body 12 may extend superiorly extra-thoracically (instead of intra-thoracically), e.g., either subcutaneously or submuscularly above the ribcage/sternum. The lead 10 may be implanted at other locations, such as over the sternum, offset to the right of the sternum, angled lateral from the proximal or distal end of the sternum, or the like.

The lead body 12 may have a generally tubular or cylindrical shape and may define a diameter of approximately 3-9 French (Fr), however, lead bodies of less than 3 Fr and more than 9 Fr may also be utilized. In another configuration, the lead body 12 may have a flat, ribbon, or paddle shape with solid, woven filament, or metal mesh structure, along at least a portion of the length of the lead body 12. In such an example, the width across the lead body 12 may be between 1-3.5 mm. Other lead body designs may be used without departing from the scope of this application.

The lead body 12 of lead 10 may be formed from a non-conductive material, including silicone, polyurethane, fluoropolymers, mixtures thereof, and other appropriate materials, and shaped to form one or more lumens (not shown), however, the techniques are not limited to such constructions. The distal portion 16 may be fabricated to be biased in a desired configuration, or alternatively, may be manipulated by the user into the desired configuration. For example, the distal portion 16 may be composed of a malleable material such that the user can manipulate the distal portion into a desired configuration where it remains until manipulated to a different configuration.

The lead body 12 may include a proximal end 14 and a distal portion 16 which include an electrical stimulation therapy portion 18 configured to deliver electrical energy to the heart or sense electrical energy of the heart. The distal portion 16 may be anchored to a desired positioned within the patient, for example, substernally or subcutaneously by, for example, suturing the distal portion 16 to the patient's musculature, tissue, or bone at the xiphoid process entry site. Alternatively, the distal portion 16 may be anchored to the patient or through the use of rigid tines, prongs, barbs, clips, screws, and/or other projecting elements or flanges, disks, pliant tines, flaps, porous structures such as a mesh-like element and metallic or non-metallic scafolds that facilitate tissue growth for engagement, bio-adhesive surfaces, and/or any other non-piercing elements.

The lead body 12 may define a substantially linear portion 20 as it curves or bends near the xiphoid process and extends superiorly. As shown in FIGS. 1-3, at least a part of the distal portion 16 may define an undulating configuration 22 distal to the substantially linear portion 20. In particular, the distal portion 16 may define an undulating pattern, e.g., (zig-zag, meandering, sinusoidal, serpentine, or other pattern) as it extends toward the distal end of the distal portion 16. In other configurations, the lead body 12 may not have a substantially linear portion 20 as it extends superiorily, but instead the undulating configuration may begin immediately after the bend.

Figure 4:
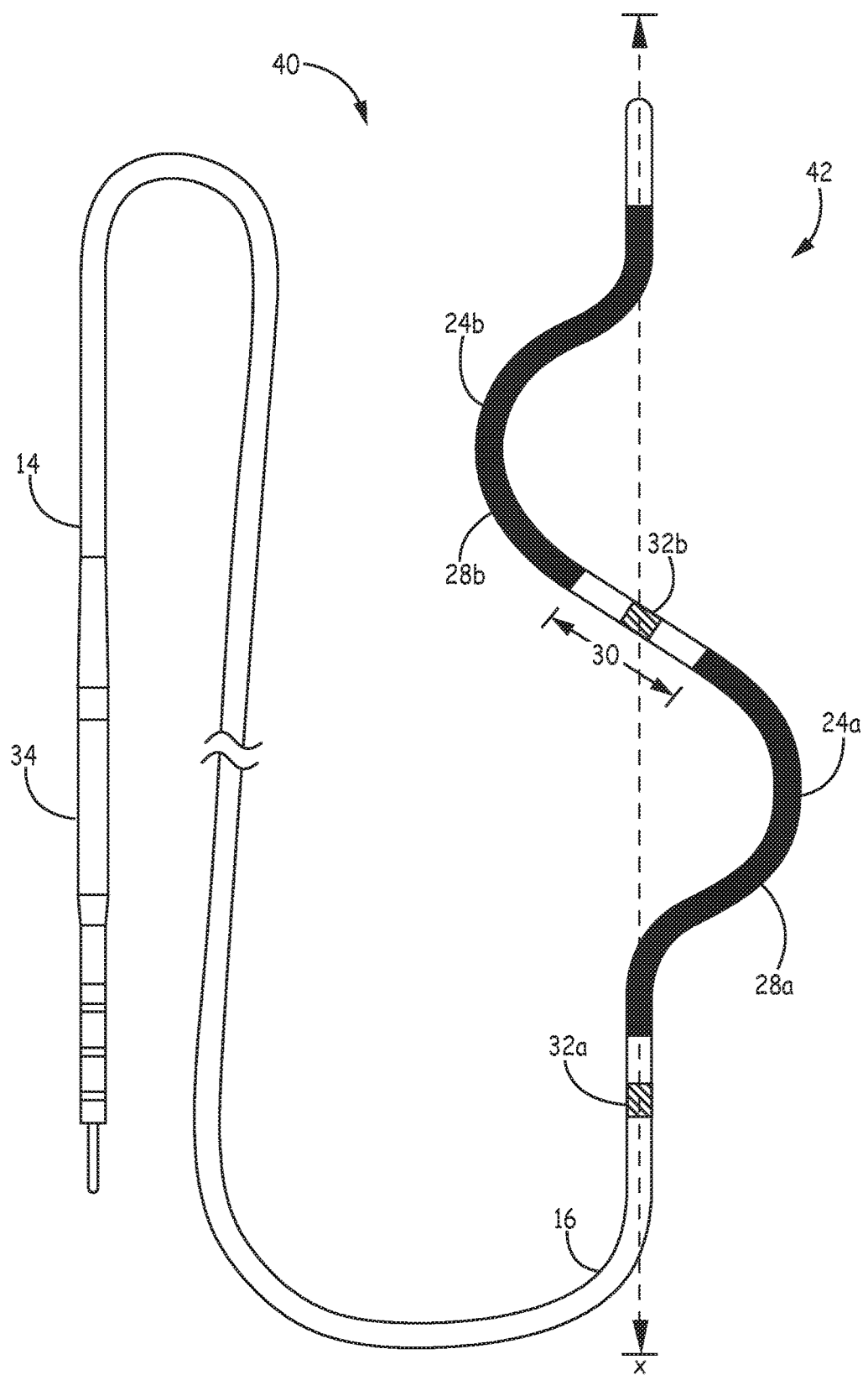
FIG. 4 is a schematic diagram illustrating another example lead constructed in accordance with the principles of the present application.
Figure 5:
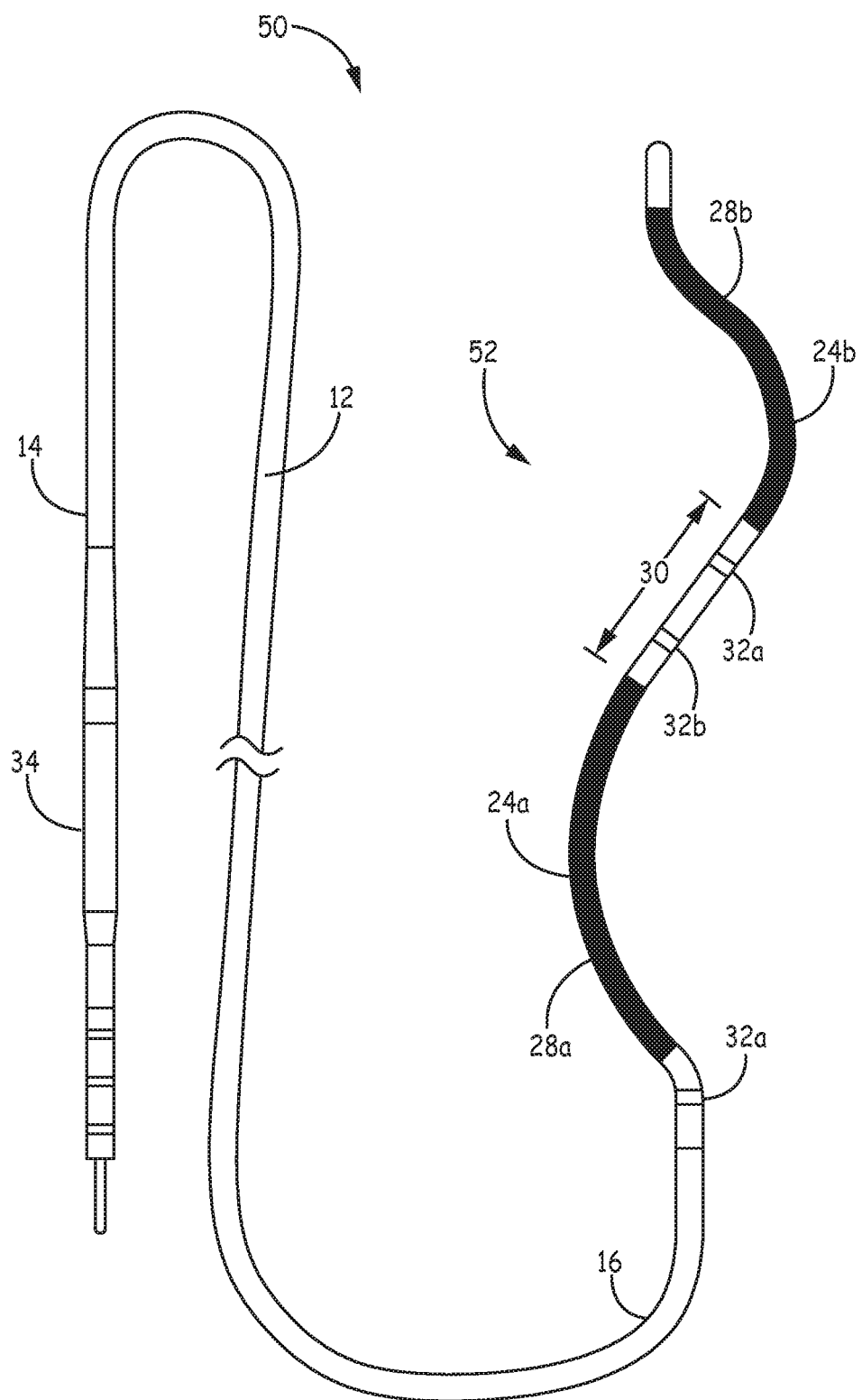
FIG. 5 is a schematic diagram illustrating a further example lead constructed in accordance with the principles of the present application.

The undulating configuration 22 may include a plurality of peaks 24 along the length of the distal portion 16. In an exemplary configuration, the undulating configuration 22 of lead 10 includes three peaks 24a, 24b, and 24c. In other configurations, however, the undulating configuration 22 may include any number of peaks 24. For example, the number of peaks 24 may be fewer or greater than three depending on the frequency of the undulation configuration 22. For example, a higher frequency undulating configuration 22 may include more peaks 24 (e.g., as illustrated in the examples illustrated in FIGS. 6-9) while a lower frequency undulating configuration 22 may include fewer peaks 24 (e.g., as illustrated in the examples of FIGS. 4 and 5).

The undulating configuration 22 may further define a peak-to-peak distance "d," (shown in FIG. 3), which may be variable or constant along the length of the undulating configuration 22. In the configuration illustrated in FIGS. 1-3, the undulating configuration 22 defines a substantially sinusoidal configuration, with a constant peak-to-peak distance "d" of approximately 2.0-5.0 cm. The undulating configuration 22 may also define a peak-to-peak width "w," (shown in FIG. 3), which may also be variable or constant along the length of the undulating configuration 22. In the configuration illustrated in FIGS. 1-3, the undulating configuration 22 defines a substantially sinusoidal shape, with a constant peak-to-peak width "w" of approximately 0.5-2.0 cm. However, in other instances, the undulating configuration 22 may define other shapes and/or patterns, e.g., S-shapes, wave shapes, or the like.

The distal portion 16 includes a defibrillation electrode 26 configured to deliver a cardioversion/defibrillation shock to the patient's heart. The defibrillation electrode 26 may include a plurality of sections or segments 28 spaced a distance apart from each other along the length of the distal portion 16. The defibrillation electrode segments 28 may be a disposed around or within the lead body 12 of the distal portion 16, or alternatively, may be embedded within the wall of the lead body 12. In one configuration, the defibrillation electrode segments 28 may be a coil electrode formed by a conductor. The conductor may be formed of one or more conductive polymers, ceramics, metal-polymer composites, semiconductors, metals or metal alloys, including but not limited to, one of or a combination of the platinum, tantalum, titanium, niobium, zirconium, ruthenium, indium, gold, palladium, iron, zinc, silver, nickel, aluminum, molybdenum, stainless steel, MP35N, carbon, copper, polyaniline, polypyrrole and other polymers. In another configuration, each of the defibrillation electrodes segments 28 may be a flat ribbon electrode, a paddle electrode, a braided or woven electrode, a mesh electrode, a directional electrode, a patch electrode or another type of electrode configured to deliver a cardioversion/defibrillation shock to the patient's heart.

In the example illustrated in FIGS. 1-3, defibrillation electrode 26 includes two sections or segments 28a and 28b, collectively 28. The defibrillation electrode segments 28 extend along a substantial part of undulating portion 22, e.g., along at least 80% of undulating portion 22. The defibrillation electrode segments 28 may extend along more or less than 80% of the undulating configuration 22. As another example, the defibrillation electrode segments 28 may extend along at least 90% of the undulating configuration 22. The defibrillation electrode segment 28a extends along a substantial portion of undulation from the proximal end of undulating portion 22 to peak 24b (e.g., along a substantial portion of the first "wave" associated with peak 24a) and the defibrillation electrode segment 28b extends along a substantial portion of undulation from peak 24b to distal end of undulating portion 22 (e.g., along a substantial portion of the second "wave" associated with peak 24c). In the example illustrated in FIGS. 1-3, the only part of undulating portion 22 that defibrillation electrode 26 is not disposed on is the gap 30 on peak 24b where electrode 32b is disposed.

In one configuration, the defibrillation electrode segments 28 are spaced approximately 0.25-4.5 cm, and in some instances between 1-3 cm apart from each other. In another configuration, the defibrillation electrode segments 28 are spaced approximately 0.25-1.5 cm apart from each other. In a further configuration, the defibrillation electrode segments 28 are spaced approximately 1.5-4.5 cm apart from each other. In the configuration shown in FIGS. 1-3, the defibrillation electrode segments 28 span a substantial part of the distal portion 16. Each of the defibrillation electrode segments 28 may be between approximately 1-10 cm in length and, more preferably, between 2-6 cm in length and, even more preferably, between 3-5 cm in length. However, lengths of greater than 10 cm and less than 1 cm may be utilized without departing from the scope of this disclosure. A total length of defibrillation electrode 26 (e.g., length of the two segments 28 combined) may vary depending on a number of variables. The defibrillation electrode 26 may, in one example, have a total length of between approximately 5-10 cm. However, the defibrillation electrode segments 24 may have a total length less than 5 cm and greater than 10 cm in other embodiments. In some instances, defibrillation segments 28 may be approximately the same length or, alternatively, different lengths.

The defibrillation electrode segments 28 may be electrically connected to one or more conductors, which may be disposed in the body wall of the lead body 12 or may alternatively be disposed in one or more insulated lumens (not shown) defined by the lead body 12. In an exemplary configuration, each of the defibrillation electrode segments 28 is connected to a common conductor such that a voltage may be applied simultaneously to all the defibrillation electrode segments 28 to deliver a defibrillation shock to a patient's heart. In other configurations, the defibrillation electrode segments 28 may be attached to separate conductors such that each defibrillation electrode segment 28 may apply a voltage independent of the other defibrillation electrode segments 28. In this case, ICD 9 or lead 10 may include one or more switches or other mechanisms to electrically connect the defibrillation electrode segments together to function as a common polarity electrode such that a voltage may be applied simultaneously to all the defibrillation electrode segments 28 in addition to being able to independently apply a voltage.

Figure 8:
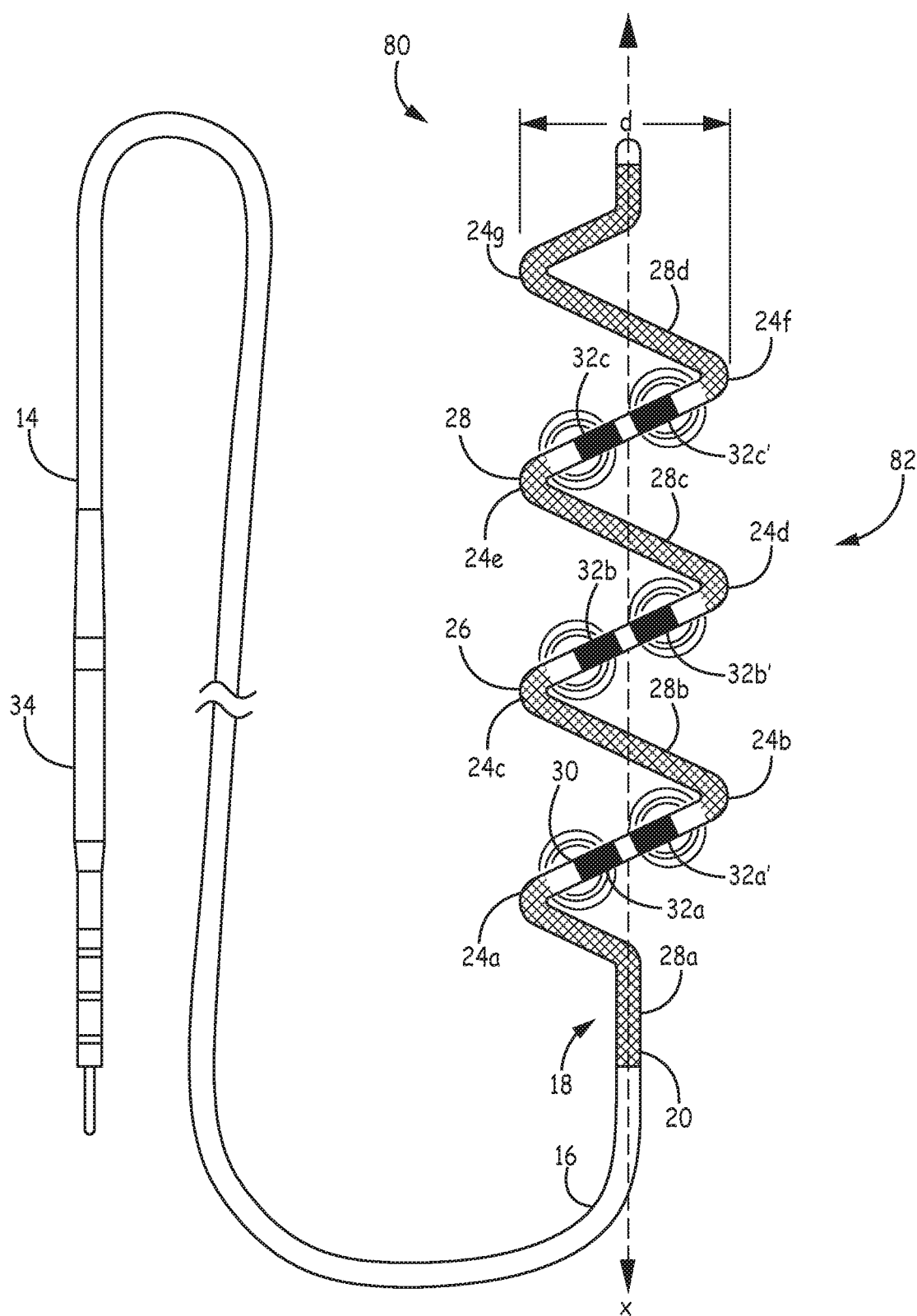
FIG. 8 is a schematic diagram illustrating another example lead constructed in accordance with the principles of the present application.

The distal portion 16 may define one or more gaps 30 between adjacent defibrillation segments 28. The gaps 30 may define any length. In instances in which more than two defibrillation segments 28 exist, each gap 30 may define the same or substantially the same length as every other gap 30 or may define a different length than other gap 30 in the distal portion. In the example of FIG. 3, a single gap 30 exists between defibrillation electrode segments 28. One or more electrodes 32 may be disposed within the respective gap 30. In the configuration shown in FIG. 1, a single electrode 32b is disposed within the gap 30. However, in other examples, more than one electrode 32 may exist within the gap 30 (e.g., as illustrated in the example of FIGS. 4 and 8). In the configuration shown in FIG. 1, another electrode 32a is located proximal to defibrillation electrode segment 28a. In other configurations, additional electrodes 32 may be disposed along the distal portion 16 of lead 10, e.g., distal to defibrillation electrode segment 28b and/or proximal to electrode segment 28a.

In one example, the distance between the closest defibrillation electrode segment 28 and electrodes 32 is greater than or equal to 2 mm and less than or equal to 1.5 cm. In another example, electrodes 32 may be spaced apart from the closest one of defibrillation electrode segments 28 by greater than or equal to 5 mm and less than or equal to 1 cm. In a further example, electrodes 32 may be spaced apart from the closest one of defibrillation electrode segments 28 by greater than or equal to 6 mm and less than or equal to 8 mm.

The electrodes 32a and 32b may be configured to deliver low-voltage electrical pulses to the heart or may sense a cardiac electrical activity, e.g., depolarization and repolarization of the heart. As such, electrodes 32 may be referred to herein as pace/sense electrodes 32. In one configuration, the electrodes 32 are ring electrodes. However, in other configurations the electrodes 32 may be any of a number of different types of electrodes, including ring electrodes, short coil electrodes, paddle electrodes, hemispherical electrodes, directional electrodes, or the like. The electrodes 32 may be the same or different types of electrodes. The electrodes 32 may be electrically isolated from an adjacent defibrillation segment 28 by including an electrically insulating layer of material between the electrodes 32 and the adjacent defibrillation segments 28. Each electrode 32 may have its own separate conductor such that a voltage may be applied to each electrode independently from another electrode 32 in the distal portion 16. In other configurations, each electrode 32 may be coupled to a common conductor such that each electrode 32 may apply a voltage simultaneously.

In the configurations shown in FIGS. 1-3, each electrode 32 is substantially aligned along a major longitudinal axis ("x"). In one example, the major longitudinal axis is defined by a portion of the elongate body 12, e.g., the substantially linear portion 20. In another example, the major longitudinal axis is defined relative to the body of the patient, e.g., along the anterior median line (or midsternal line), one of the sternal lines (or lateral sternal lines), left parasternal line, or other line. The electrodes 32a and 32b may be disposed along the undulating configuration 22 such that each electrode 32a and 32b is substantially aligned or otherwise disposed along the major longitudinal axis "x." In one configuration, the midpoint of each electrode 32a and 32b is along the major longitudinal axis "x," such that each electrode 32a and 32b is at least disposed at substantially the same horizontal position when the distal portion is implanted within the patient. In other configurations, the electrodes 32 may be disposed at any longitudinal or horizontal position along the distal portion 16 disposed between, proximal to, or distal to the defibrillation electrode segments 28, as described in other embodiments herein. In the example illustrated in FIGS. 1-3, the electrodes 32 are disposed along the undulating configuration 22 at locations that will be closer to the heart of the patient than defibrillation electrode segments 28 (e.g., at peak 24b that is toward the left side of the sternum). As illustrated in FIG. 1A, for example, the electrodes 32 are substantially aligned with one another along the left sternal line. The defibrillation electrode segments 28 are disposed along the peaks 24a and 24c that extend toward a right side of the sternum away from the heart. This configuration places the pace/sense electrodes 32 at locations closer to the heart and thereby lower pacing thresholds and better sense cardiac activity of the heart.

As illustrated in longitudinal side view of distal portion 16 of FIG. 3B, the pace/sense electrodes 32 and the defibrillation electrode segments 28 may further be disposed in a common plane when the distal portion 16 is implanted extracardiovascularly. In particular, the undulating configuration 22 is substantially disposed in a plane defined by the longitudinal axis "x" and a horizontal axis ("y"), referred to herein as the horizontal plane (e.g., the x-y plane). In the example illustrated in FIG. 3B, each defibrillation electrode segment 28 and each electrode 32 is at least partially disposed in the horizontal plane. Optionally, in other configurations, the undulating configuration 22 may not be substantially disposed in the horizontal plane. Instead, the electrical stimulation therapy portion 18 may be curved such that one or more the defibrillation electrode segments 28 or pace/sense electrodes 32 may be pressed inward toward the heart. For example, the electrical stimulation therapy portion 18 may define a concavity or a curvature to place the one or more of the defibrillation electrode segments 28 or the pace/sense electrodes 32 close to the heart. In such case, the undulating portion 22 may be viewed as being a 3-dimensional serpentine shape in which some of the peaks or portions of the peaks 24 extend in the z-direction, perpendicular to the horizontal plane and toward the heart.

The proximal end 14 of the lead body 12 may include one or more connectors 34 to electrically couple the lead 10 to the implantable cardioverter-defibrillator (ICD) 9 subcutaneously implanted within the patient, for example, under the left armpit of the patient. The ICD 9 may include a housing 38 that forms a hermetic seal which protects the components of ICD 9. The housing 38 of ICD 9 may be formed of a conductive material, such as titanium or titanium alloy, which may function as a housing electrode for a particular therapy vector as illustrated by the arrows in FIG. 1 between the housing 38 and the distal portion 16. The ICD 36 may also include a connector assembly that includes electrical feedthroughs through which electrical connections are made between the one or more connectors 34 of lead 10 and the electronic components included within the housing 38. The housing 38 may house one or more processors, memories, transmitters, receivers, sensors, sensing circuitry, therapy circuitry, power sources (capacitors and batteries) and/or other appropriate components. The components of ICD 9 may generate and deliver electrical stimulation therapy such as anti-tachycardia pacing, cardioversion or defibrillation shocks, post-shock pacing, bradycardia pacing, or other electrical stimulation.

The particular configuration of the undulating configuration 22 and the inclusion of the electrodes 32 between defibrillation electrode segments 28 provides a number of therapy vectors for the delivery of electrical stimulation therapy to the heart. For example, as shown in FIGS. 1-3, at least a portion of the defibrillation electrode 26 and one of the electrodes 32 may be disposed over the right ventricle, or any chamber of the heart, such that pacing pulses and defibrillation shocks may be delivered to the heart from the therapy portion 18. The housing 38 may be charged with or function as a polarity different than the polarity of the one or more defibrillation electrode segments 28 and/or electrodes 32 such that electrical energy may be delivered between the housing 38 and the defibrillation electrode segment(s) 28 and/or electrode(s) 32 to the heart. Each defibrillation electrode segment 28 may have the same polarity as every other defibrillation electrode segment 28 when a voltage is applied to it such that a defibrillation shock may be delivered from the entirety of the defibrillation electrode 26. In embodiments in which defibrillation electrode segments 28 are electrically connected to a common conductor within lead body 12, this is the only configuration of defibrillation electrode segments 28. However, in other embodiments, defibrillation electrode segments 28 may be coupled to separate conductors within lead body 12 and may therefore each have different polarities such that electrical energy may flow between defibrillation electrode segments 28 (or between one of defibrillation electrode segments 28 and one or pace/sense electrodes 32 or the housing electrode) to provide pacing therapy and/or to sense cardiac depolarizations. In this case, the defibrillation electrode segments 28 may still be electrically coupled together (e.g., via one or more switches within ICD 9) to have the same polarity to deliver a defibrillation shock from the entirety of the defibrillation electrode 26.

Additionally, each electrode 32 may be configured to conduct electrical pulses directly to the heart, or sense a cardiac depolarization between adjacent defibrillation electrode segments 28, whether disposed on the same defibrillation electrode segment 28 or on other defibrillation electrode segment 28, and/or between proximate electrodes 32. For example, the therapy vector lines shown in FIG. 3 illustrate the flow of electrical energy between the electrodes 32a and 32b and adjacent defibrillation electrode segments 28. The therapy vector lines illustrate potential vectors that can be generated to target specific areas of the heart for electrical stimulation therapy or to target different areas of the heart so as to be able to select a pacing and/or sensing vector with best performance (e.g., lowest pacing capture thresholds). Additionally electrodes 32 may conduct electrical pulses between one another, e.g., between one of electrodes 32 and an inferior and superior electrode 32, between one of electrodes 32 and the housing electrode, or between a plurality of electrodes 32 (at the same polarity) and the housing electrode at the opposite polarity. As such, each electrode 32 may have the same polarity as every other electrode 32 or alternatively, may have different polarities such that different therapy vectors can be utilized to deliver pacing pulses to the heart.

FIG. 4 is a schematic diagram illustrating another example lead 40 constructed in accordance with the principles of the present application. Lead 40 can include one or more of the structure and/or functionality of lead 10 of FIGS. 1-3 (and vice versa), including the electrode and lead body dimensions, spacings, materials, shapes, orientations, electrical conductor configurations, and the like. Repetitive description of like numbered elements described in other embodiments is omitted for sake of brevity.

Lead 40 includes an undulating portion 42. Undulating portion 42 is substantially similar to undulating portion 22 of lead 10, but undulating portion 42 includes only two peaks 24. However, undulating portion 42 may define a peak-to-peak distance "d" and peak-to-peak width "w" with similar dimensions described above with respect to FIGS. 1-3.

Lead 40 includes a defibrillation electrode 26 formed from two defibrillation electrode segments 28a and 28b. The defibrillation electrode segments 28 extend along a substantial part of undulating portion 42, e.g., along at least 80% of undulating portion 42. The defibrillation electrode segment 28a extends along a substantial portion of undulation from the proximal end of undulating portion 42, except for the part of undulating portion 42 that includes the gap 30 where electrode 32b is disposed. In the example illustrated in FIG. 4, the gap 30 and electrode 32b are located along the part of undulating portion 42 that transitions from peak 24a to peak 24b, instead of at a peak as was the case in lead 10 of FIGS. 1-3.

Lead 40 also includes two pace/sense electrodes 32a and 32b. The electrodes 32a and 32b are disposed along the undulating configuration 42 such that each electrode 32a and 32b is substantially aligned or otherwise disposed along the major longitudinal axis "x." Unlike in lead 10 of FIGS. 1-3, however, the orientation of electrodes 32a and 32b are different even though they are substantially disposed at substantially the same horizontal position when the distal portion is implanted within the patient. Moreover, electrodes 32 are disposed along the undulating configuration 42 at locations such that the electrodes 32 will be substantially aligned with one another along the anterior median line instead of the left sternal line. In this case, the defibrillation electrode segment 28a is disposed along the peak 24a and will extend toward the left side of the sternum when implanted and defibrillation electrode segment 28b is disposed along the peak 24b and will extend toward the right side of the sternum when implanted.

Defibrillation electrode segments 28 and pace/sense electrodes 32 may include the structure and functionality described above with respect to FIGS. 1-3, including but not limited to the spacing between segments 28 and electrodes 32, the size of segments 28 and 32, electrode and lead body dimensions, spacings, materials, shapes, and the like. Additionally, as described above with respect to FIGS. 1-3, in some configurations defibrillation electrode segments 28 may each be connected to a common conductor such that a voltage may be applied simultaneously to all the defibrillation electrode segments 28 (and they function as a single polarity) to deliver a defibrillation shock to a patient's heart. In other configurations, the defibrillation electrode segments 28 may be attached to separate conductors such that each defibrillation electrode segment 28 may apply a voltage independent of the other defibrillation electrode segments 28. In this case, ICD 9 or lead 40 may include one or more switches or other mechanisms to electrically connect the defibrillation electrode segments together to function as a common polarity electrode such that a voltage may be applied simultaneously to all the defibrillation electrode segments 28 in addition to being able to independently apply a voltage.

FIG. 5 is a schematic diagram illustrating another example lead 50 constructed in accordance with the principles of the present application. Lead 50 can include one or more of the structure and/or functionality of lead 10 of FIGS. 1-3 (and vice versa) or lead 40 of FIG. 4, including the electrode and lead body dimensions, spacings, materials, shapes, orientations, electrical conductor configurations, and the like. Repetitive description of like numbered elements described in other embodiments is omitted for sake of brevity.

Lead 50 includes an undulating portion 52. Undulating portion 52 includes two peaks 24, similar to undulating portion 42 of lead 40, but undulating portion 52 includes a longer peak-to-peak width "w." Lead 50 also includes three pace/sense electrodes 32 with two of them being disposed between defibrillation electrode segments 28. Unlike the example leads illustrated in FIGS. 1-4, at least one of the pace/sense electrodes 32 is not substantially aligned or otherwise disposed along the major longitudinal axis "x."

Figure 6:
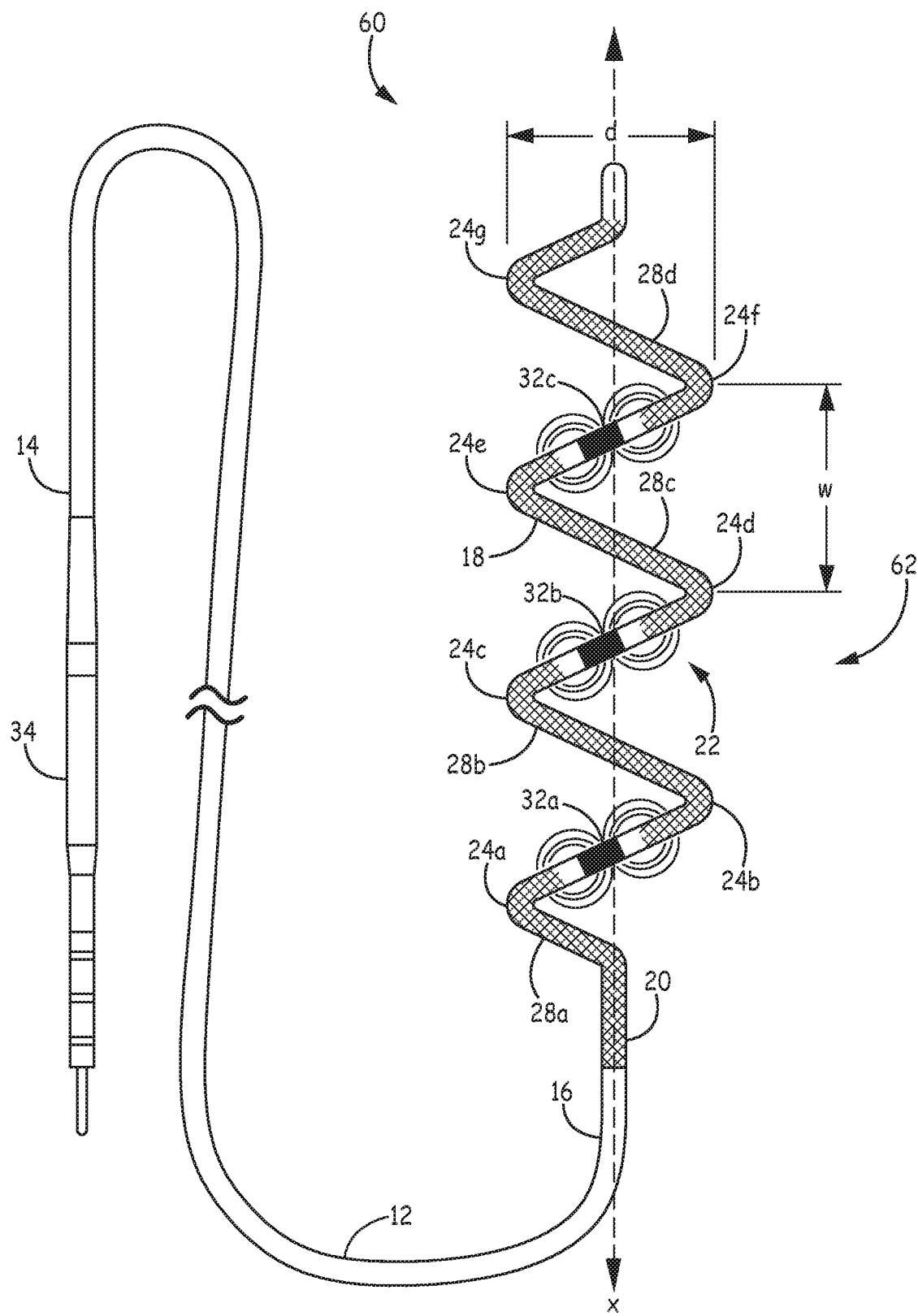
FIG. 6 is a schematic diagram illustrating another example lead constructed in accordance with the principles of the present application.

FIG. 6 is a schematic diagram illustrating another example lead 60 constructed in accordance with the principles of the present application. Lead 60 can include one or more of the structure and/or functionality of lead 10 of FIGS. 1-3, lead 40 of FIG. 4, and/or lead 50 of FIG. 5 (and vice versa), including the electrode and lead body dimensions, spacings, materials, shapes, orientations, electrical conductor configurations, and the like. Repetitive description of like numbered elements described in other embodiments is omitted for sake of brevity.

Lead 60 includes an undulating portion 62. Undulating portion 62 is substantially similar to undulating portion 22 of lead 10, but undulating portion 62 includes seven peaks 24a-g instead of three peaks. Undulating portion 62 defines a peak-to-peak distance "d" with similar dimensions described above with respect to FIGS. 1-3, but the peak-to-peak width "w" may be smaller than the peak-to-peak widths of undulating portions 22, 42, or 52 due to the increased number of peaks 24.

The defibrillation electrode also includes more defibrillation electrode segments 28 than the leads 10, 40 and 50. The defibrillation electrode segments 28 extend along a substantial part of undulating portion 62, e.g., along at least 80% of undulating portion 62. The defibrillation electrode segments 28 extend along a substantial portion of undulation from the proximal end of undulating portion 62, except for the part of undulating portion 62 that includes the gaps 30 where electrodes 32 are disposed. In the example illustrated in FIG. 6, the gaps 30 and electrodes 32b are located along the part of undulating portions 62 that transition from a peak 24 to adjacent peak 24 (at every other transition), instead of at a peak as was the case in lead 10 of FIGS. 1-3.

Lead 60 also includes three pace/sense electrodes 32a-32c. The electrodes 32 are disposed along the undulating configuration 62 such that each electrode 32 is substantially aligned or otherwise disposed along the major longitudinal axis "x." Unlike in lead 10, 40 and 50 of FIGS. 1-5, however, all electrodes 32 are located between adjacent defibrillation electrode segments 28. In other instances, the lead 60 may also include one or more electrodes 32 proximal to the most proximal defibrillation electrode segment 28 or distal to the most distal defibrillation electrode segment 28. Electrodes 32 are disposed along the undulating configuration 62 at locations such that the electrodes 32 will be substantially aligned with one another along the anterior median line.

Defibrillation electrode segments 28 and pace/sense electrodes 32 may include the structure and functionality described above with respect to FIGS. 1-3, including but not limited to the spacing between segments 28 and electrodes 32, the size of segments 28 and 32, electrode and lead body dimensions, spacings, materials, shapes, and the like. Additionally, as described above with respect to FIGS. 1-3, in some configurations defibrillation electrode segments 28 may each be connected to a common conductor such that a voltage may be applied simultaneously to all the defibrillation electrode segments 28 (and they function as a single polarity) to deliver a defibrillation shock to a patient's heart. In other configurations, the defibrillation electrode segments 28 may be attached to separate conductors such that each defibrillation electrode segment 28 may apply a voltage independent of the other defibrillation electrode segments 28. In this case, ICD 9 or lead 60 may include one or more switches or other mechanisms to electrically connect the defibrillation electrode segments together to function as a common polarity electrode such that a voltage may be applied simultaneously to all the defibrillation electrode segments 28 in addition to being able to independently apply a voltage.

Figure 7:
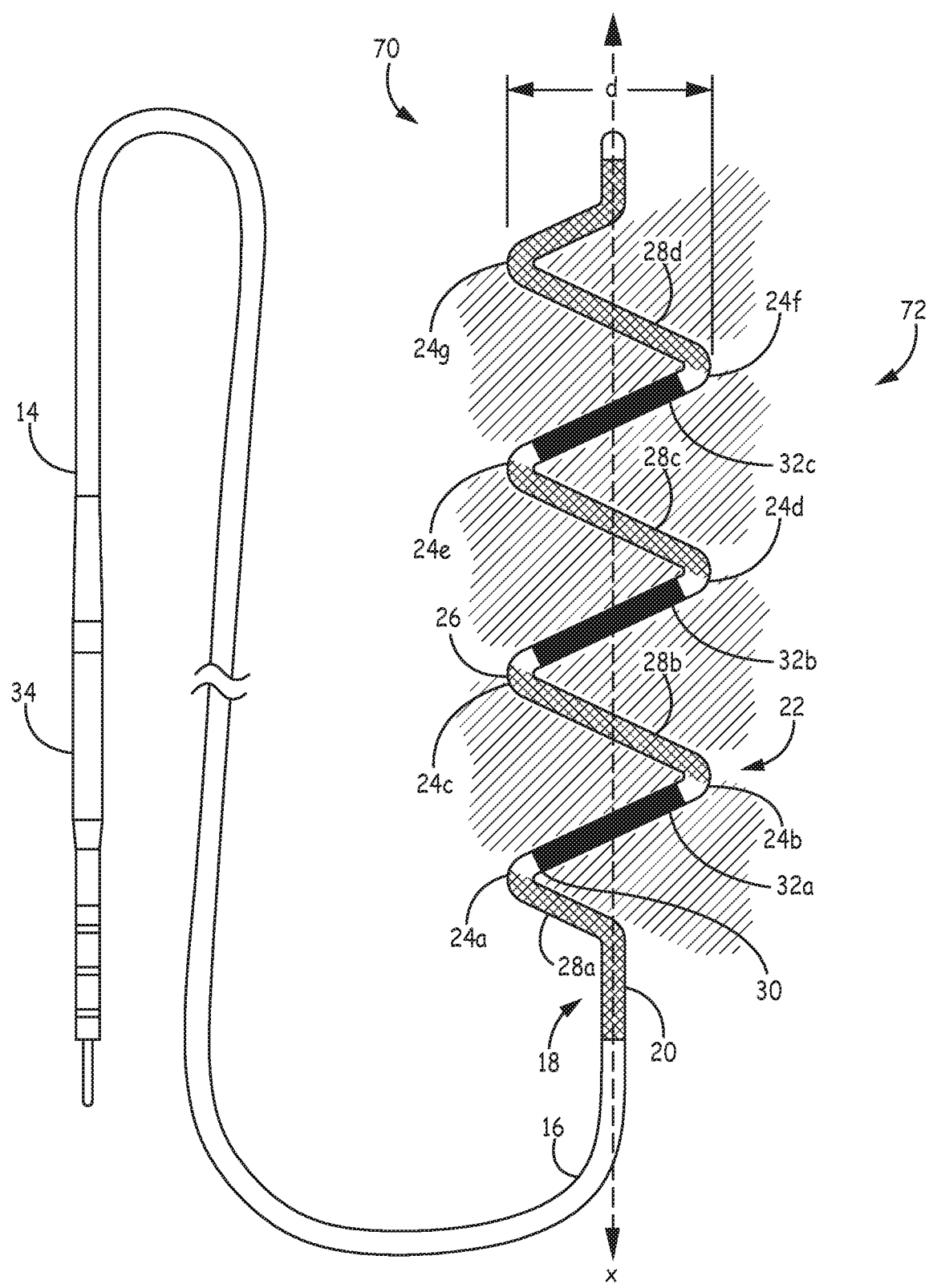
FIG. 7 is a schematic diagram illustrating another example lead constructed in accordance with the principles of the present application.

FIG. 7 is a schematic diagram illustrating another example lead 70 constructed in accordance with the principles of the present application. Lead 70 can include one or more of the structure and/or functionality of lead 10 of FIGS. 1-3, lead 40 of FIG. 4, lead 50 of FIG. 5 and/or lead 60 of FIG. 6 (and vice versa), including the electrode and lead body dimensions, spacings, materials, shapes, orientations, electrical conductor configurations, and the like. Repetitive description of like numbered elements described in other embodiments is omitted for sake of brevity.

Lead 70 includes an undulating portion 72 that is substantially similar to undulating portion 62 of lead 60 of FIG. 6 except that the electrode 32 may be sized to span the distance between two peaks 24 in the undulating configuration 72. In this configuration, the electrodes 32 may be configured to sense a cardiac depolarization between an adjacent defibrillation electrode segment 28. Moreover, the electrodes 32 are configured to deliver pacing pulses to the heart by conductive electrical energy between the electrodes 32 and an adjacent defibrillation electrode segment 28. In such a configuration, the therapy vectors between a respective electrode 32 and an adjacent defibrillation electrode segment 28 may define a substantially rhomboid or diamond configuration to provide for a particular therapy vector. Electrodes 32 may also deliver electrical energy between respective ones of electrodes 32. Repetitive description of like numbered elements described in other embodiments is omitted for the sake of brevity.

FIG. 8 is a schematic diagram illustrating another example lead 80 constructed in accordance with the principles of the present application. Lead 80 can include one or more of the structure and/or functionality of lead 10 of FIGS. 1-3, lead 40 of FIG. 4, lead 50 of FIG. 5 lead 60 of FIG. 6, and/or lead 70 of FIG. 7 (and vice versa), including the electrode and lead body dimensions, spacings, materials, shapes, orientations, electrical conductor configurations, and the like. Repetitive description of like numbered elements described in other embodiments is omitted for sake of brevity.

Lead 80 includes an undulating portion 82 that may conform substantially to undulating portion 62 of lead 60 of FIG. 6 and/or undulating portion 72 of lead 70 of FIG. 7 except that two or more electrodes 32 may span the distance between two peaks 24 in the undulating configuration 62. The electrodes 32 may be disposed in a single gap 30 between adjacent defibrillation electrode segments 28 or each electrode 32 may be disposed in a two gaps 30 and each gap 30 is separated by an electrically insulating section of the lead body 12. In the configuration shown in FIG. 8, the electrodes 32 may be configured to sense a cardiac depolarization between each other or an adjacent defibrillation electrode segment 28, depending on the polarity of each electrode 32. Moreover, the electrodes 32 are configured to deliver pacing pulses to the heart with conductive electrical energy between the electrodes 32 and an adjacent defibrillation electrode segment 28 or between two of the electrodes 32. For example, therapy vectors are shown in FIG. 8 for a configuration in which, for example, electrodes 32a and 32a' have the same polarity and the opposite polarity of an adjacent defibrillation electrode segment 28 to provide for a particular therapy vector. However, electrodes 32a and 32a', and likewise 32b and 32b' and 32c, and 32c' may be coupled to the same or different conductors such that the polarities between each electrode 32 may be the same or different depending on the application. Between each electrode 32a and 32a', for example, may be a portion of the lead body 12 that is electrically insulating. Moreover, the gaps 30 may be sized to optimize particular electrical stimulation therapies. For example, the gap 30 size may range from approximately 8 mm-15 mm for between a pair of electrodes 32 configured to pace and/or sense a cardiac depolarization. Additionally, the size of the gaps 30 between an electrode 32 and a defibrillation electrode segment 28 may be approximately 3-10 mm in length or any of the lengths described above with respect to FIGS. 1-3. Repetitive description of like numbered elements described in other embodiments is omitted for sake of brevity.

Figure 9:
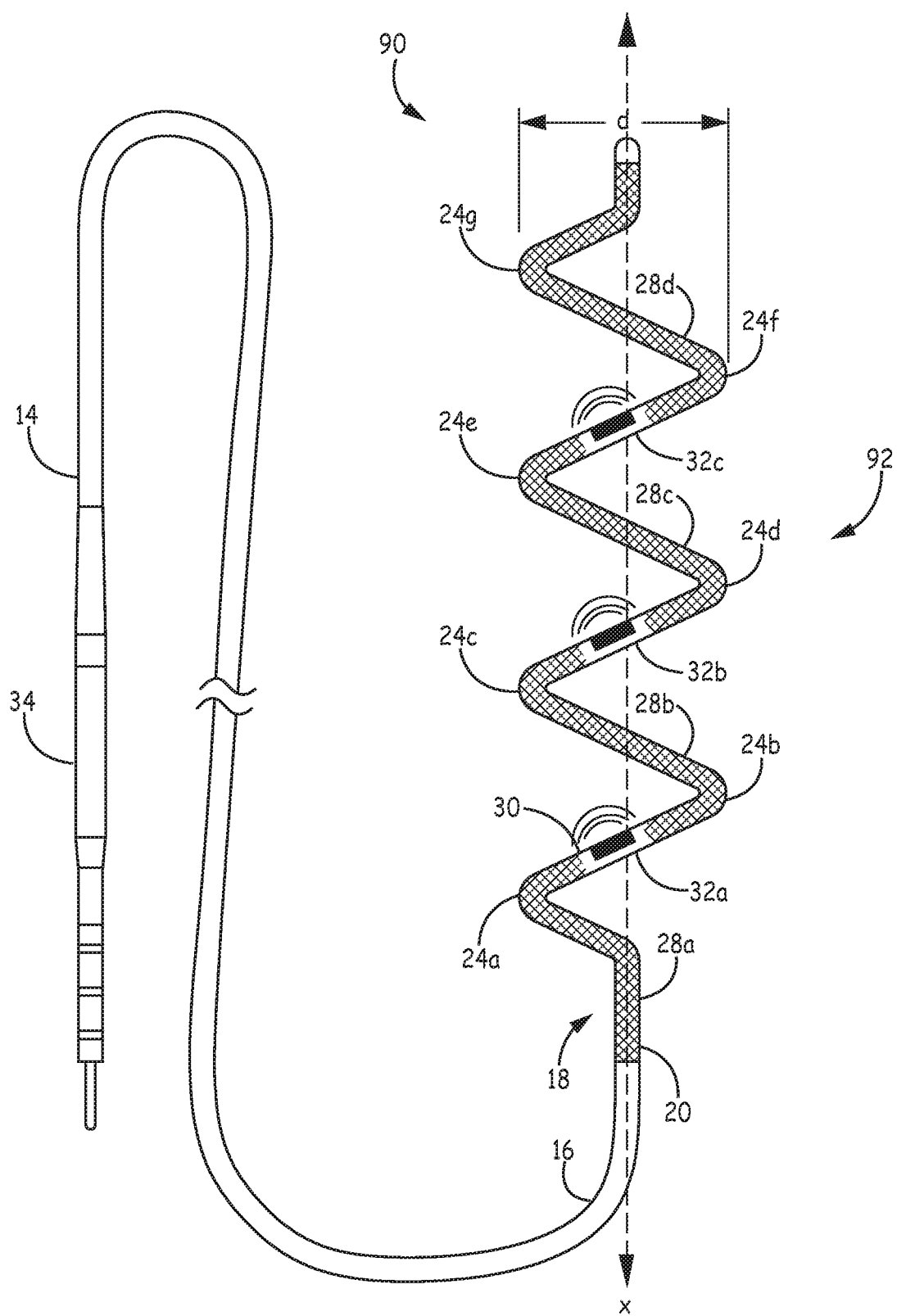
FIG. 9 is a schematic diagram illustrating another example lead constructed in accordance with the principles of the present application.

FIG. 9 is a schematic diagram illustrating another example lead 90 constructed in accordance with the principles of the present application. Lead 90 can include one or more of the structure and/or functionality of lead 10 of FIGS. 1-3, lead 40 of FIG. 4, lead 50 of FIG. 5 and/or lead 60 of FIG. 6, lead 70 of FIG. 7, and/or lead 80 of FIG. 8 (and vice versa), including the electrode and lead body dimensions, spacings, materials, shapes, orientations, electrical conductor configurations, and the like. Repetitive description of like numbered elements described in other embodiments is omitted for sake of brevity.

Lead 90 includes an undulating portion 92 that may conform substantially to undulating portion 62 of lead 60 of FIG. 6 except that electrodes 32 may be directional electrodes positioned to provide a therapy vector aimed at the heart and not skeletal muscle, such that only a portion of the lead body in which the electrodes 32 are disposed contain the electrode 32 and another portion includes the insulating portion of the lead body. The electrodes 32 would be arranged such that the electrodes are disposed on the posterior side of the lead (e.g., facing the heart) when implanted within the patient. In this configuration, the electrodes 32 may be configured to sense a cardiac depolarization between an adjacent defibrillation electrode segment 28, between two of electrodes 32, or between electrode(s) 32 and housing electrode. Moreover, the electrodes 32 are configured to deliver pacing pulses to the heart by conductive electrical energy between an adjacent defibrillation electrode segment 28, between two of electrodes 32, or between electrode(s) 32 and housing electrode. For example, therapy vectors are shown in FIG. 6 for a configuration in which each electrode 32a, 32b, and 32c are disposed on the superior portion of a lead body 62 section. In other configurations, for example, electrodes 32a and 32c may be facing electrode 32b to provide for particular therapy vectors. The arrangement of electrodes 32a, 32b, and 32c may be such that electrical energy is directed toward the heart and not toward skeletal muscle or non-cardiac tissue to maximize the effectiveness of pacing pulses delivered to the heart. Repetitive description of like numbered elements described in other embodiments is omitted for sake of brevity.

Figure 10:
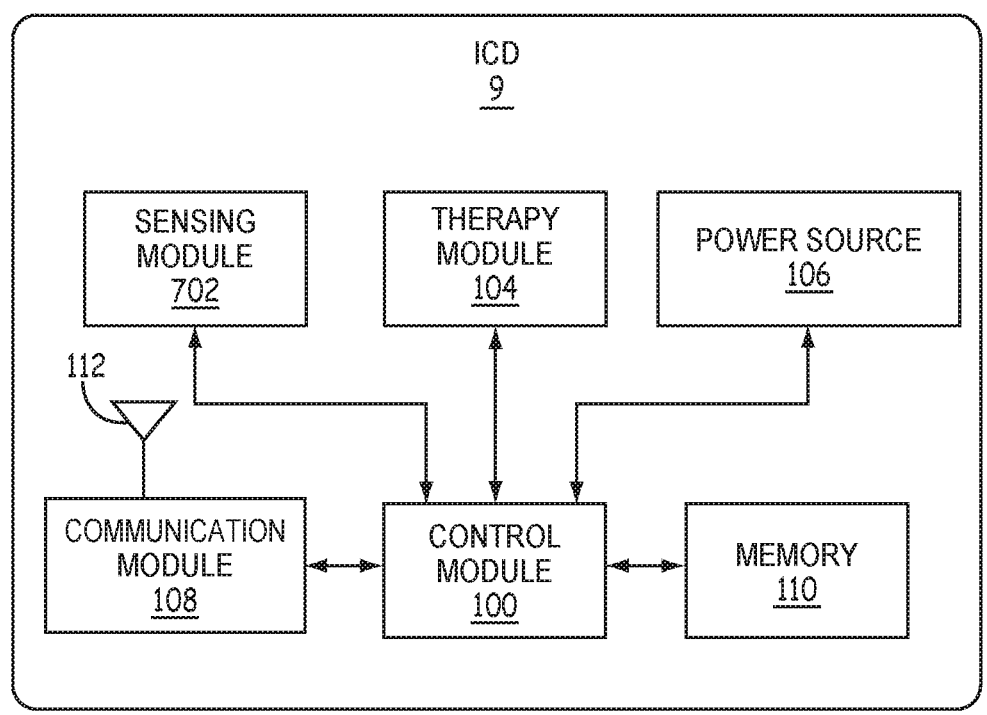
FIG. 10 is a functional block diagram of an example configuration of electronic components of an example ICD, such as the ICD of the system in FIGS. 1A, 1C, and 2.

FIG. 10 is a functional block diagram of an example configuration of electronic components of an example ICD 9. ICD 9 includes a control module 100, sensing module 102, therapy module 104, communication module 108, and memory 110. The electronic components may receive power from a power source 106, which may be a rechargeable or non-rechargeable battery. In other embodiments, ICD 9 may include more or fewer electronic components. The described modules may be implemented together on a common hardware component or separately as discrete but interoperable hardware or software components. Depiction of different features as modules is intended to highlight different functional aspects and does not necessarily imply that such modules must be realized by separate hardware or software components. Rather, functionality associated with one or more modules may be performed by separate hardware or software components, or integrated within common or separate hardware or software components. FIG. 10 will be described in the context of ICD 9 being coupled to lead 10 for exemplary purposes only. However, ICD 9 may be coupled to other leads, such as lead 40, 50, 60, 70, 80 or 90 described herein, and thus other electrodes.

Sensing module 102 is electrically coupled to some or all of electrodes 26 (or separately to segments 28a and/or 28b) and 32 via the conductors of lead 10 and one or more electrical feedthroughs, or to the housing electrode via conductors internal to the housing of ICD 9. Sensing module 102 is configured to obtain signals sensed via one or more combinations of electrodes 26 (or separately to segments 28a and/or 28b) and 32 and the housing electrode of ICD 9 and process the obtained signals.

The components of sensing module 102 may be analog components, digital components or a combination thereof. Sensing module 102 may, for example, include one or more sense amplifiers, filters, rectifiers, threshold detectors, analog-to-digital converters (ADCs) or the like. Sensing module 102 may convert the sensed signals to digital form and provide the digital signals to control module 100 for processing or analysis. For example, sensing module 102 may amplify signals from the sensing electrodes and convert the amplified signals to multi-bit digital signals by an ADC. Sensing module 102 may also compare processed signals to a threshold to detect the existence of atrial or ventricular depolarizations (e.g., P- or R-waves) and indicate the existence of the atrial depolarization (e.g., P-waves) or ventricular depolarizations (e.g., R-waves) to control module 100.

Control module 100 may process the signals from sensing module 102 to monitor electrical activity of the heart of the patient. Control module 100 may store signals obtained by sensing module 102 as well as any generated EGM waveforms, marker channel data or other data derived based on the sensed signals in memory 110. Control module 100 may analyze the EGM waveforms and/or marker channel data to detect cardiac events (e.g., tachycardia). In response to detecting the cardiac event, control module 100 may control therapy module 104 to deliver the desired therapy to treat the cardiac event, e.g., defibrillation shock, cardioversion shock, ATP, post-shock pacing, or bradycardia pacing.

Therapy module 104 is configured to generate and deliver electrical stimulation therapy to the heart. Therapy module 104 may include one or more pulse generators, capacitors, and/or other components capable of generating and/or storing energy to deliver as pacing therapy, defibrillation therapy, cardioversion therapy, cardiac resynchronization therapy, other therapy or a combination of therapies. In some instances, therapy module 104 may include a first set of components configured to provide pacing therapy and a second set of components configured to provide defibrillation therapy. In other instances, therapy module 104 may utilize the same set of components to provide both pacing and defibrillation therapy. In still other instances, therapy module 104 may share some of the defibrillation and pacing therapy components while using other components solely for defibrillation or pacing.

Control module 100 may control therapy module 104 to deliver the generated therapy to the heart via one or more combinations of electrodes 26 (or separately to segments 28a and/or 28b) and 32 of lead 10 and the housing electrode of ICD 9 according to one or more therapy programs, which may be stored in memory 110. In instances in which control module 100 is coupled to a different lead, e.g., lead 40, 50, 60, 70, 80, or 90, other electrodes may be utilized. Control module 100 controls therapy module 104 to generate electrical stimulation therapy with the amplitudes, pulse widths, timing, frequencies, electrode combinations or electrode configurations specified by a selected therapy program.

Therapy module 104 may include a switch module to select which of the available electrodes are used to deliver the therapy. The switch module may include a switch array, switch matrix, multiplexer, or any other type of switching device suitable to selectively couple electrodes to therapy module 104. Control module 100 may select the electrodes to function as therapy electrodes, or the therapy vector, via the switch module within therapy module 104. In instances in which defibrillation segments 28a and 28b are each coupled to separate conductors, control module 100 may be configured to selectively couple therapy module 104 to either one of segments 28a and 28b individually or couple to both of the segments 28a and 28b concurrently. In some instances, the same switch module may be used by both therapy module 104 and sensing module 102. In other instances, each of sensing module 102 and therapy module 104 may have separate switch modules.

In the case of pacing therapy being provided, e.g., ATP, post-shock pacing, and/or bradycardia pacing provided via electrodes 32 and/or defibrillation electrode segments 28a and 28b of lead 10. In one example, therapy module 104 may deliver pacing (e.g., ATP or post-shock pacing) using an electrode vector that includes one or both defibrillation electrode segments 28a and 28b. The electrode vector used for pacing may be segment 28a as an anode (or cathode) and one of electrodes 28b, 32 or the housing of ICD 9 as the cathode (or anode) or segment 28b as an anode (or cathode) and one of electrodes 28b, 32 or the housing of ICD 9 as the cathode (or anode). If necessary, therapy module 104 may generate and deliver a cardioversion/defibrillation shock (or shocks) using one or both of electrode segments 28 concurrently as a cathode and the housing electrode of ICD 9 as an anode.

Control module 100 controls therapy module 104 to generate and deliver pacing pulses with any of a number of shapes, amplitudes, pulse widths, or other characteristic to capture the heart. For example, the pacing pulses may be monophasic, biphasic, or multi-phasic (e.g., more than two phases). The pacing thresholds of the heart when delivering pacing pulses from the substernal space, e.g., from electrodes 32 and/or electrode segments 28 substantially within anterior mediastinum 36, may depend upon a number of factors, including location, type, size, orientation, and/or spacing of electrodes 32 and/or electrode segments 28, location of ICD 9 relative to electrodes 32 and/or electrode segments 28, physical abnormalities of the heart (e.g., pericardial adhesions or myocardial infarctions), or other factor(s).

The increased distance from electrodes 32 and/or electrode segments 28 of lead 10 to the heart tissue may result in the heart having increased pacing thresholds compared to transvenous pacing thresholds. To this end, therapy module 104 may be configured to generate and deliver pacing pulses having larger amplitudes and/or pulse widths than conventionally required to obtain capture via leads implanted within the heart (e.g., transvenous leads) or leads attached directly to the heart. In one example, therapy module 104 may generate and deliver pacing pulses having amplitudes of less than or equal to 8 volts and pulse widths between 0.5-3.0 milliseconds and, in some instances up to 4 milliseconds. In another example, therapy module 104 may generate and deliver pacing pulses having amplitudes of between 5 and 10 volts and pulse widths between approximately 3.0 milliseconds and 10.0 milliseconds. In another example, therapy module 104 may generate and deliver pacing pulses having pulse widths between approximately 2.0 milliseconds and 8.0 milliseconds. In a further example, therapy module 104 may generate and deliver pacing pulses having pulse widths between approximately 0.5 milliseconds and 20.0 milliseconds. In another example, therapy module 104 may generate and deliver pacing pulses having pulse widths between approximately 1.5 milliseconds and 20.0 milliseconds.

Pacing pulses having longer pulse durations than conventional transvenous pacing pulses may result in lower energy consumption. As such, therapy module 104 may be configured to generate and deliver pacing pulses having pulse widths or durations of greater than two (2) milliseconds. In another example, therapy module 104 may be configured to generate and deliver pacing pulses having pulse widths or durations of between greater than two (2) milliseconds and less than or equal to three (3) milliseconds. In another example, therapy module 104 may be configured to generate and deliver pacing pulses having pulse widths or durations of greater than or equal to three (3) milliseconds. In another example, therapy module 104 may be configured to generate and deliver pacing pulses having pulse widths or durations of greater than or equal to four (4) milliseconds. In another example, therapy module 104 may be configured to generate and deliver pacing pulses having pulse widths or durations of greater than or equal to five (5) milliseconds. In another example, therapy module 104 may be configured to generate and deliver pacing pulses having pulse widths or durations of greater than or equal to ten (10) milliseconds. In a further example, therapy module 104 may be configured to generate and deliver pacing pulses having pulse widths between approximately 3-10 milliseconds. In a further example, therapy module 104 may be configured to generate and deliver pacing pulses having pulse widths between approximately 4-10 milliseconds. In a further example, therapy module 104 may be configured to generate and deliver pacing pulses having pulse widths or durations of greater than or equal to fifteen (15) milliseconds. In yet another example, therapy module 104 may be configured to generate and deliver pacing pulses having pulse widths or durations of greater than or equal to twenty (20) milliseconds.

Depending on the pulse widths, ICD 9 may be configured to deliver pacing pulses having pulse amplitudes less than or equal to twenty (20) volts, deliver pacing pulses having pulse amplitudes less than or equal to ten (10) volts, deliver pacing pulses having pulse amplitudes less than or equal to five (5) volts, deliver pacing pulses having pulse amplitudes less than or equal to two and one-half (2.5) volts, deliver pacing pulses having pulse amplitudes less than or equal to one (1) volt. In other examples, the pacing pulse amplitudes may be greater than 20 volts. Typically the lower amplitudes require longer pacing widths as illustrated in the experimental results. Reducing the amplitude of pacing pulses delivered by ICD 9 reduces the likelihood of extra-cardiac stimulation and lower consumed energy of power source 106.

For pacing therapy provided from the subcutaneous placement of lead 10 above the sternum and/or ribcage, pacing amplitudes and pulse widths may vary, e.g., be increased given the further distances from heart and the various anatomical features via which the energy must penetrate.

In the case of cardioversion or defibrillation therapy, e.g., cardioversion or defibrillation shocks provided by defibrillation electrode segments 28 (individually or together), control module 100 controls therapy module 104 to generate cardioversion or defibrillation shocks having any of a number of waveform properties, including leading-edge voltage, tilt, delivered energy, pulse phases, and the like. Therapy module 104 may, for instance, generate monophasic, biphasic or multiphasic waveforms. Additionally, therapy module 104 may generate cardioversion or defibrillation waveforms having different amounts of energy. As with pacing, delivering cardioversion or defibrillation shocks from the substernal space, e.g., from electrode segment(s) 28 substantially within anterior mediastinum 36, may reduce the amount of energy that needs to be delivered to defibrillate the heart. When lead 10 is implanted in the substernal space, therapy module 104 may generate and deliver cardioversion or defibrillation shocks having energies of less than 65 J, less than 100 J, between 40-50 J, between 35-100 J, and in some instances less than 35 J. When lead 10 is implanted subcutaneously, ICD 9 may generate and deliver cardioversion or defibrillation shocks having energies around 65-80 J.

Therapy module 104 may also generate defibrillation waveforms having different tilts. In the case of a biphasic defibrillation waveform, therapy module 104 may use a 65/65 tilt, a 50/50 tilt, or other combinations of tilt. The tilts on each phase of the biphasic or multiphasic waveforms may be the same in some instances, e.g., 65/65 tilt. However, in other instances, the tilts on each phase of the biphasic or multiphasic waveforms may be different, e.g., 65 tilt on the first phase and 55 tilt on the second phase. The example delivered energies, leading-edge voltages, phases, tilts, and the like are provided for example purposes only and should not be considered as limiting of the types of waveform properties that may be utilized to provide sub sternal defibrillation via defibrillation electrode segment(s) 28.

Communication module 108 includes any suitable hardware, firmware, software or any combination thereof for communicating with another device, such as a clinician programmer, a patient monitoring device, or the like. For example, communication module 108 may include appropriate modulation, demodulation, frequency conversion, filtering, and amplifier components for transmission and reception of data with the aid of antenna 112. Antenna 112 may be located within connector block of ICD 9 or within housing ICD 9.

The various modules of ICD 9 may include any one or more processors, controllers, digital signal processors (DSPs), application specific integrated circuits (ASICs), field-programmable gate arrays (FPGAs), or equivalent discrete or integrated circuitry, including analog circuitry, digital circuitry, or logic circuitry. Memory 110 may include computer-readable instructions that, when executed by control module 100 or other component of ICD 9, cause one or more components of ICD 9 to perform various functions attributed to those components in this disclosure. Memory 110 may include any volatile, non-volatile, magnetic, optical, or electrical media, such as a random access memory (RAM), read-only memory (ROM), non-volatile RAM (NVRAM), static non-volatile RAM (SRAM), electrically-erasable programmable ROM (EEPROM), flash memory, or any other non-transitory computer-readable storage media.

The leads and systems described herein may be used at least partially within the substernal space, e.g., within anterior mediastinum of patient, to provide an extravascular ICD system. An implanter (e.g., physician) may implant the distal portion of the lead intra-thoracically using any of a number of implant tools, e.g., tunneling rod, sheath, or other tool that can traverse the diagrammatic attachments and form a tunnel in the substernal location. For example, the implanter may create an incision near the center of the torso of the patient, e.g., and introduce the implant tool into the substernal location via the incision. The implant tool is advanced from the incision superior along the posterior of the sternum in the substernal location. The distal end of lead 10 (or other lead described herein, e.g., leads 40, 50, 60, 70, 80, or 90) is introduced into tunnel via implant tool (e.g., via a sheath). As the distal end of lead 10 is advanced through the substernal tunnel, the distal end of lead 10 is relatively straight. The pre-formed or shaped undulating portion 22 is flexible enough to be straightened out while routing the lead 10 through a sheath or other lumen or channel of the implant tool. Once the distal end of lead 10 is in place, the implant tool is withdrawn toward the incision and removed from the body of the patient while leaving lead 10 in place along the substernal path. As the implant tool is withdrawn, the distal end of lead 10 takes on its pre-formed undulating configuration 22. Thus, as the implant tool is withdrawn, the undulating configuration 22 pushes electrodes 32a and 32b toward the left side of sternum compared to electrodes 28a and 28b. As mentioned above, the implanter may align the electrodes 32a and 32b along the anterior median line (or midsternal line) or the left sternal lines (or left lateral sternal line).

It will be appreciated by persons skilled in the art that the present application is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the application, which is limited only by the following claims.

The invention claimed is:

1. An implantable medical electrical lead comprising:
a lead body defining a proximal end and a distal portion, wherein at least a part of the distal portion of the lead body defines an undulating configuration;
a defibrillation electrode that includes a plurality of defibrillation electrode segments disposed along the undulating configuration, wherein each defibrillation electrode segment of the plurality of defibrillation electrode segments is spaced apart from each adjacent defibrillation electrode segment of the plurality of defibrillation electrode segments by a respective distance, and wherein the plurality of defibrillation electrode segments are disposed to cover at least 80% of the undulating configuration; and
at least one electrode disposed between adjacent segments of the plurality of defibrillation electrode segments, the at least one electrode configured to perform at least one of:
deliver a pacing pulse to a heart; or
sense cardiac electrical activity of the heart.

2. The lead of claim 1, wherein the plurality of defibrillation electrode segments are disposed to cover at least 90% of the undulating configuration.

3. The lead of claim 1, wherein the undulating configuration includes a plurality of peaks, a first portion of the plurality of peaks extending in a first direction away from a major longitudinal axis of the lead and a second portion of the plurality of peaks extending in a second, opposite direction away from the major longitudinal axis of the lead, wherein the plurality of defibrillation electrode segments are disposed along the first portion of the plurality of peaks and the at least one electrode is disposed on the second portion of the plurality of peaks.

4. The lead of claim 3, wherein the plurality of peaks of the undulating configuration are within a common plane.

5. The lead of claim 3, wherein at least one of the plurality of peaks of the undulating configuration is not in a common plane with the other ones of the plurality of peaks of the undulating configuration.

6. The lead of claim 1, wherein the undulating configuration includes a plurality of peaks, a first portion of the plurality of peaks extending in a first direction away from a major longitudinal axis of the lead and a second portion of the plurality of peaks extending in a second, opposite direction away from the major longitudinal axis of the lead, wherein the plurality of defibrillation electrode segments are disposed to cover at least a portion of the plurality of peaks and the at least one electrode is disposed along a portion of the undulating portion between peaks.

7. The lead of claim 1, further including a conductor disposed within the lead body, wherein the plurality of defibrillation electrode segments are electrically coupled to the conductor.

8. The lead of claim 7, further including a connector disposed at the proximal end of the lead body, the connector being configured to electrically couple with an electrical energy generator, and wherein the conductor is coupled to the connector.

9. The lead of claim 1, wherein the plurality of defibrillation electrode segments includes a first defibrillation electrode segment and a second defibrillation electrode segment, the lead further comprising:
a first conductor disposed within the lead body and electrically connected to the first defibrillation electrode segment; and
a second conductor disposed within the lead body and electrically connected to the second defibrillation electrode segment.

10. The lead of claim 1, wherein the at least one electrode comprises at least two electrodes, wherein the at least two electrodes are disposed along a major longitudinal axis of the lead.

11. The lead of claim 1, wherein the undulating configuration defines a substantially sinusoidal configuration.

12. The lead of claim 1, wherein the at least one electrode is configured to conduct electrical pulses between an adjacent one of the plurality of defibrillation electrode segments.

13. The lead of claim 1, further comprising at least one additional electrode that is disposed at least one of:
proximal to a most proximal one of the defibrillation electrode segments; or
distal to a most distal one of the defibrillation electrode segments, the at least one additional electrode configured to perform at least one of:
deliver a pacing pulse to the heart; or
sense cardiac electrical activity of the heart.

14. The lead of claim 13, wherein the at least one additional electrode is not disposed along the undulating configuration.

15. An extravascular implantable cardioverter-defibrillator (ICD) system comprising:
an extravascular electrical stimulation lead that includes:
a lead body defining a proximal end and a distal portion, wherein at least a part of the distal portion of the lead body defines an undulating configuration;
a defibrillation electrode that includes at least a first defibrillation electrode segment and a second defibrillation electrode segment disposed along the undulating configuration spaced apart from one another by a distance, wherein the first defibrillation electrode segment and the second defibrillation electrode segment are disposed to cover at least 80% of the undulating configuration; and
at least one electrode disposed between the first and second defibrillation electrode segments, the at least one electrode configured to perform at least one of:
deliver a pacing pulse to a heart; or
sense cardiac electrical activity of the heart; and
an implantable cardioverter defibrillator (ICD) coupled to the extravascular electrical stimulation lead, the ICD including:
a therapy module configured to generate and deliver electrical stimulation therapy; and
a switch module configured to selectively couple the therapy module to an electrode vector in which both the first and second defibrillation electrode segments simultaneously function at a common polarity to deliver defibrillation therapy.

16. The extravascular ICD system of claim 15, wherein the undulating configuration includes a plurality of peaks, a first portion of the plurality of peaks extending in a first direction away from a major longitudinal axis of the lead and a second portion of the plurality of peaks extending in a second, opposite direction away from the major longitudinal axis of the lead, wherein the first and second defibrillation electrode segments are disposed along respective ones of the first portion of the plurality of peaks and the at least one electrode is disposed on the second portion of the plurality of peaks.

17. The extravascular ICD system of claim 15, wherein the undulating configuration includes a plurality of peaks, a first portion of the plurality of peaks extending in a first direction away from a major longitudinal axis of the lead and a second portion of the plurality of peaks extending in a second, opposite direction away from the major longitudinal axis of the lead, wherein the first defibrillation electrode segment is disposed along one of the first portion of peaks extending in the first direction, the second defibrillation electrode segment is disposed along one of the second portion of peaks extending in the second direction, and the at least one electrode is disposed along a segment of the undulating portion between two adjacent peaks.

18. The extravascular ICD system of claim 15, wherein the electrode vector is a first electrode vector, and wherein the switch module couples the therapy module to a second electrode vector that includes at least one of the first and second defibrillation electrode segments and the therapy module delivers a pacing therapy using the second electrode vector.

19. The extravascular ICD system of claim 18, wherein the second electrode vector includes the first defibrillation electrode segment as a first polarity of the second electrode vector and the second defibrillation electrode segment as a second, opposite polarity of the second electrode vector.

20. An implantable medical electrical lead comprising:
a lead body defining a proximal end and a distal portion, wherein at least a part of the distal portion of the lead body defines an undulating configuration comprising one or more undulations;
a defibrillation electrode that includes a plurality of defibrillation electrode segments disposed along the undulating configuration wherein each defibrillation electrode segment of the plurality of defibrillation electrode segments is spaced apart from each adjacent defibrillation electrode segment of the plurality of defibrillation electrode segments by a respective distance, and wherein each defibrillation electrode segment of the plurality of defibrillation electrode segments is disposed to cover greater than half of a respective undulation of the one or more undulations; and
at least one electrode disposed between adjacent segments of the plurality of defibrillation electrode segments, the at least one electrode configured to perform at least one of:
deliver a pacing pulse to a heart; or
sense cardiac electrical activity of the heart.

21. A method of implanting an extravascular electrical stimulation lead within a substernal location of a patient, the method comprising:
creating an incision near a center of the torso of the patient;
introducing an implant tool into the substernal location via the incision;
advancing the implant tool within the substernal location from the incision superior along a posterior of a sternum to form a substernal path;
introducing a distal portion of the lead into the substernal location, the lead including a lead body defining a proximal end and a distal portion, wherein at least a part of the distal portion of the lead body defines a pre-formed undulating configuration, and comprising a defibrillation electrode that includes a plurality of defibrillation electrode segments disposed along the undulating configuration, wherein each defibrillation electrode segment of the plurality of defibrillation electrode segments is spaced apart from each adjacent defibrillation segment of the plurality of defibrillation segments by a respective distance, and wherein the plurality of defibrillation electrode segments are disposed to cover at least 80% of the undulating configuration, and wherein lead further comprises at least one electrode disposed between adjacent segments of the plurality of defibrillation segments, the at least one electrode configured to perform at least one of deliver a pacing pulse to the heart or sense cardiac electrical activity of the heart;
advancing the distal portion of the lead through the substernal path, wherein the undulating configuration of the lead is in a relatively straight configuration when being advanced through the substernal path;
withdrawing the implant tool toward the incision to remove the implant tool from the body while leaving the lead in place along the substernal path, wherein the distal portion of the lead takes its pre-formed undulating configuration within the substernal location as it exits the implant tool, and wherein the at least one electrode is disposed on the undulating configuration such that that undulating configuration pushes the at least one electrode toward the left side of the sternum compared to the defibrillation electrode segments.

22. The method of claim 21, wherein the at least one electrode is located along an anterior median line of the patient and the defibrillation electrode segments are located toward a right sternal line of the patient.

23. The method of claim 21, wherein the at least one electrode is located along a left sternal line of the patient and the defibrillation electrode segments are located toward a right sternal line of the patient.

* * * * *